US012734201B2

(12) United States Patent
Espadaler Mazo et al.

(10) Patent No.: US 12,734,201 B2
(45) Date of Patent: Sep. 15, 2026

(54) PROBIOTIC COMPOSITION FOR THE TREATMENT OF COVID-19

(71) Applicant: AB-BIOTICS, S.A., Sant Cugat del Valles (ES)

(72) Inventors: Jordi Espadaler Mazo, Sant Cugat del Valles (ES); Ariana Salavert Larrosa, Sant Cugat del Valles (ES); Sergi Audivert Brugué, Sant Cugat del Valles (ES); Miquel Àngel Bonachera Sierra, Sant Cugat del Valles (ES)

(73) Assignee: AB-BIOTICS, S.A., Sant Cugat del Valles (ES)

( * ) Notice: Subject to any disclaimer, the term of this patent is extended or adjusted under 35 U.S.C. 154(b) by 364 days.

(21) Appl. No.: 18/264,703

(22) PCT Filed: Feb. 11, 2022

(86) PCT No.: PCT/EP2022/053332
§ 371 (c)(1),
(2) Date: Aug. 8, 2023

(87) PCT Pub. No.: WO2022/171779
PCT Pub. Date: Aug. 18, 2022

(65) Prior Publication Data

US 2024/0226199 A1 Jul. 11, 2024

Related U.S. Application Data

(63) Continuation of application No. PCT/EP2021/053539, filed on Feb. 12, 2021.

(51) Int. Cl.

| | |
|---|---|
| ***A61K 35/747*** | (2015.01) |
| ***A61P 31/14*** | (2006.01) |
| ***A61P 37/04*** | (2006.01) |

(52) U.S. Cl.
CPC ............ *A61K 35/747* (2013.01); *A61P 31/14* (2018.01); *A61P 37/04* (2018.01)

(58) Field of Classification Search
None
See application file for complete search history.

(56) References Cited

FOREIGN PATENT DOCUMENTS

WO WO-2011092261 A1 * 8/2011 .............. A61P 37/02

OTHER PUBLICATIONS

Dictionary definition "improve": https://www.merriam-webster.com/dictionary/improve retrieved Mar. 4, 2026.*

Anonymous, "History of Changes for Study: NCT04517422", Jan. 30, 2021 (Jan. 30, 2021), XP055816388, Retrieved from the Internet: URL: https://clinicaltrials.gov/ct2/history/NCT04517422?V_6=View#StudyPageTop [retrieved on Jun. 22, 2021] the whole document.

Spagnolello Ornella, et al., "Targeting Microbiome: An Alternative Strategy for Fighting SARS-CoV-2 Infection", Chemotherapy, vol. 66, No. 1-2 Jan. 1, 2021 (Jan. 1, 2021), pp. 24-32, XP055816387, CH ISSN: 0009-3157, DOI: 10.1159/000515344 Retrieved from the Internet: URL: https://www.karger.com/Article/Pdf/515344 the whole document; table 1.

Baindara P., et al., "Oral probiotics in coronavirus disease 2019: connecting the gut-lung axis to viral pathogenesis, inflammation, secondary infection and clinical trials", New Microbes and New Infections vol. 40 Jan. 6, 2021 (Jan. 6, 2021), p. 100837, XP055816389, GB ISSN: 2052-2975, DOI: 10.1016/j.nmni.2021.100837 Retrieved from the Internet: URL: https://www.ncbi.nlm.nih.gov/pmc/articles/PMC7785423/pdf/main.pdf.

Gutierrez-Castrellon Pedro, et al., "Efficacy and safety of novel probiotic formulation in adult Covid19 outpatients: a randomized, placebo-controlled clinical trial", medRxiv, May 24, 2021 (May 24, 2021), XP055816390, DOI: 10.1101/2021.05.20.21256954 Retrieved from the Internet: URL: https://www.medrxiv.org/content/10.1101/2021.05.20.21256954v1.full.pdf [retrieved on Jun. 22, 2021] the whole document.

Hu Jielun, et al., "Review article: Probiotics, prebiotics and dietary approaches during COVID-19 pandemic", Trends in Food Science and Technology, Elsevier Science Publishers, GB, vol. 108, Dec. 31, 2020 (Dec. 31, 2020), pp. 187-196, XP086473321, ISSN: 0924-2244, DOI: 10.1016/J.TIFS.2020.12.009 [retrieved on Dec. 31, 2020] the whole document.

Loren Violeta, et al., "Comparative Effect of the 13.1 Probiotic Formula in Two Animal Models of Colitis", Probiotics and Antimicrobial Proteins, New York, NY ; Heidelberg : Springer, New York, NY ; Heidelberg : Springer, vol. 9, No. 1, Nov. 10, 2016 (Nov. 10, 2016), pp. 71-80, XP036191555,ISSN: 1867-1306, DOI: 10.1007/S12602-016-9239-5; [retrieved on Nov. 10, 2016] the whole document.

(Continued)

*Primary Examiner* — Oluwatosin A Ogunbiyi
(74) *Attorney, Agent, or Firm* — Colson Law Group, PLLC

(57) ABSTRACT

A probiotic composition comprising *Lactobacillus plantarum* CECT 30292, *Lactobacillus plantarum* CECT 7484, *Lactobacillus plantarum* CECT 7485, and *Pediococcus acidilactici* CECT 7483 is provided. The probiotic composition is useful in treating, preventing, or ameliorating CO VID-19, and other infectious diseases. It is also useful in enhancing the immune response.

3 Claims, 7 Drawing Sheets

Specification includes a Sequence Listing.

(56) References Cited

OTHER PUBLICATIONS

Darbandi Atieh, et al., "The effect of probiotics on respiratory tract infection with special emphasis on COVID-19: Systemic review 2010-20", International Journal of Infectious Diseases, International Society for Infectious Diseases, Hamilton, CA, vol. 105, Feb. 9, 2021 (Feb. 9, 2021), pp. 91-104, XP086576980, ISSN: 1201-9712, DOI: 10.1016/J.IJID.2021.02.011 [retrieved on Feb. 9, 2021] the whole document.

Anonymous: "Immune Health I Ab-Biotics", Jun. 22, 2021 (Jun. 22, 2021), XP055816666, Retrieved from the Internet: URL: https://www.ab-biotics.com/products/immune-health/ [retrieved on Jun. 22, 2021] the whole document.

Anonymous: "Un probi6tico de cuatro cepas bacterianas aumenta anticuerpos IgG e IgM en pacientes positives para el COVID-19—Aula de la farmacia", Jul. 15, 2021 (Jul. 15, 2021), XP055847380, Retrieved from the Internet: URL: https://www.auladelafarmacia.com/probiotico-cepas-bacterianas-anticuerpos-pacientes-covid/ [retrieved on Oct. 4, 2021] the whole document.

* cited by examiner

PROBIOTIC COMPOSITION FOR THE TREATMENT OF COVID-19

FIELD OF THE INVENTION

The present invention relates to the fields of medicine and microbiology and particularly, to a probiotic composition to benefit human and animal health, particularly useful in the treatment of COVID-19 disease and other infectious diseases, and to increase antibodies directed at the SARSCoV-2 virus.

REFERENCE TO SEQUENCE LISTING APPENDIX

The present application includes a sequence listing appendix. The appendix contains an ASCII text file including a sequence listing, which listing is incorporated by reference in its entirety as follows:

REPLACEMENT 03-11-2024.txt 4,219,000 bytes Created Mar. 11, 2024

BACKGROUND ART

At the filing date of the present application, the webpage clinicaltrials.gov (clinicaltrials. gov/ct2/show/NCT04517422) discloses the design of a clinical trial with identifier NCT04517422 with title "Efficacy of *L. plantarum* and *P. acidilactici* in adults with SARS-CoV-2 and COVID-19". This disclosure was published Aug. 18, 2020. The sponsor and responsible party (the provider of the information) is AB-Biotics, S.A. The applicant of the present application is also AB-Biotics, S.A. Therefore, the discussed webpage publication may be considered as so-called "inventor originated disclosure" (i.e., the subject matter in the public disclosure must be attributable to the inventor, one or more co-inventors, or another who obtained the subject matter directly or indirectly from the inventor or a co-inventor).

The above-mentioned webpage publication reads (emphasis added): "Randomized controlled trial (RCT) to evaluate safety and efficacy of *Lactobacillus plantarum* CECT 7481, *Lactobacillus plantarum* CECT 7484, *Lactobacillus plantarum* CECT 7485 y *P. acidilactici* CECT 7483, one dose a day to reduce the risk of subjects with mild COVID-19 to evolute to moderate or severe disease."

Intervention Model Description: Randomized controlled trials. 300 subjects (18-60 years old) will be allocated to receive a combination of *Lactobacillus plantarum* CECT7481, *Lactobacillus plantarum* CECT 7484, *Lactobacillus plantarum* CECT 7485, and *P. acidilactici* CECT 7483 (branch one) or placebo (branch two)." "Experimental: Probiotics Active test product contains four lactic acid bacteria strains with Qualified Presumption of Safety (QPS) status by European Food Safety Authority (EFSA): *Lactobacillus plantarum* CECT 7481, *Lactobacillus plantarum* CECT 7484, *Lactobacillus plantarum* CECT 7485, and *Pediococcus acidilactici* CECT 7483 . . . ."

The present application relates to the combination of *Lactobacillus plantarum* CECT 30292 (also referred in this description as DSM 33765), *Lactobacillus plantarum* CECT 7484, *Lactobacillus plantarum* CECT 7485 and *Pediococcus acidilactici* CECT 7483. This combination is not disclosed in the above-mentioned publication at the filing date of the present patent application.

With respect to use of a probiotic composition for the treatment of COVID-19, the above-mentioned publication does not disclose any significant experimental data, i.e., the combination related statements may be seen as mere statements that are not supported by any significant verifiable experimental data.

WO2011092261A1 discloses a probiotic composition formed by *L. plantarum* CECT 7484, *L. plantarum* CECT 7485 y *P. acidilactici* CECT 7483 for the treatment of gastrointestinal diseases or conditions such as Inflammatory Bowel Disease, Irritable Bowel Syndrome or abdominal distension and bloating.

Coronavirus Disease-19 (COVID-19) is caused by the novel coronavirus 2 (SARS-CoV-2, formerly known as 2019-nCoV). SARS-CoV-2 infection may be asymptomatic or it may cause a wide spectrum of symptoms, ranging from mild symptoms (e.g., mild-to-moderate dyspnoea, fever and/or headache, with non-pneumonia or mild pneumonia) to severe symptoms (e.g., severe dyspnoea, partial pressure of arterial oxygen to fraction of inspired oxygen ratio <300, and/or severe pneumonia), sometimes up until critical symptoms (e.g., respiratory failure, septic shock, and/or multiple organ dysfunction or failure leading to death). Particularly, low arterial oxygen saturation has been repeatedly shown to be a risk factor for disease progression and later death, regardless of other symptoms.

Therefore, in order to avoid progression to more severe disease, it is of great interest to ensure fast remission of mild individuals, which constitute the majority of cases. However, effective treatments for people with mild to moderate disease have been more ambiguous. For instance, the anti-inflammatory effect of corticosteroids has been found beneficial in severe COVID-19, but it is thought its effects could actually worsen clinical outcomes in patients with mild or moderate disease.

Strains of *L. plantarum* have been previously shown to be beneficial in respiratory infections. [Chong et al. 2019], However, it has been clearly shown that effect intensity of different strains of *L. plantarum* on immune cells has a wide range of variation [Meijerink et al. 2010], A recent study has reported that drug therapy (hydroxychloroquine, antibiotics, and tocilizumab, alone or in combination) along with a probiotic mixture shortens the overall duration of symptoms in patients positive for COVID-19, who already showed moderate-to-severe symptoms and had required hospitalization. Further, the study was not randomized, and no effects on disease remission, reduction of viral load or potentiation of antibody response were reported in this study [D'Ettorre et al. 2020], Strain *P. acidilactici* K15 was also recently studied for prevention of common cold and influenza in preschool children during the common cold and influenza season. However, limited effects were reported in the study, since the probiotic was unable to shorten the duration of fever or the incidence of influenza in the overall study population, and only managed to shorten the duration of fever in those subjects who consumed very few fermented foods. Moreover, this probiotic was unable 5 to boost the levels of antibodies specific for influenza. [Hishiki et al. 2020], Probiotic features are strain-dependent, even among bacteria of the same species.

Therefore, it is important to find those strains that have a better performance in all probiotic requirements. In particular, immunological effects are considered to be rare among probiotics, and thus highly strain-10 specific [Hill et al. 2014], In view of the above, it is of great interest to find new therapies for subjects suffering from mild to moderate symptoms of COVID-19 in order to avoid progression to more severe disease.

SUMMARY OF THE INVENTION

Working examples herein provide detailed experimental data demonstrating significant positive effects in relation to the use of the probiotic compositions disclosed herein for the treatment of COVID-19 in a human patient.

Example 2 shows that the probiotic compositions disclosed herein significantly increase the rate of complete remission of the disease (at day 30 of intervention). Further, symptomatic remission is achieved earlier in patients receiving the probiotic composition. Particularly, the probiotic composition significantly reduces viral load in nasopharyngeal swabs during intervention, and is reduced 925 times on average (i.e., almost 1 log) at day 30 of intervention. Furthermore, the probiotic composition enhances the production of antibodies resulting in a significantly higher concentration of IgG and IgM. Finally, the duration of various specific symptoms of COVID-19 (e.g., fever, cough, headache, shortness of breath, bodily pain, hypoxemia and diarrhea) is significantly reduced in patients receiving the probiotic composition.

Example 3 shows on the one hand that serum concentration of interferon-beta was significantly increased in the probiotic group compared to placebo both after 15 days and 30 days of intervention. Type I interferons (interferon alpha and interferon beta) are proteins with the ability to restrict viral replication in vertebrate cells. Besides this direct antiviral effect, type-I interferons also have an 35 indirect antiviral effect, by means of stimulating B lymphocytes (B-cells) and Natural Killer lymphocytes (NK-cells). B-cells produce virus-specific antibodies that prevent viral spread by binding to viral particles.

Therefore, type-I interferons have a broad-spectrum antiviral activity. Accordingly, an impaired 40 type-I interferon response in humans is associated to a more severe disease upon lung infection by a variety of viruses, particularly coronaviruses such as SARS-CoV2, SARS-CoV1 (SARS) and MERS-CoV (MERS), but also influenza virus, human rhinovirus or respiratory syncytial virus, and even non-pulmonary viral infections like hepatitis C virus or brain infection (encephalitis) caused by herpes simplex virus [Channapannavar et al. 2019; Haagmans et al. 2004], Therefore, the skilled in the art will recognize the usefulness of the probiotic composition provided herein able to increase interferon-beta in patients to treat diseases where higher type-I interferons can be beneficial, particularly viral infections, particularly respiratory viral infections, more particularly lung viral infections.

On the other hand, Example 3 also shows that serum concentration of CXCL13 was significantly reduced over time in the probiotic group compared to placebo. CXCL13 is a protein which is induced by type-I interferons during viral infections and helps to start recruiting B-cells to infection sites. However, CXCL13 has a strong pro-inflammatory effect and is associated to lung damage across a wide spectrum of conditions, from COVID-19 to Lung Fibrosis and Chronic Obstructive Pulmonary Disease. Of note, blockade of CXCL13 has been shown to limit such lung damage.

Viral respiratory pathogens known to induce CXCL13 include SARS-COV2, influenza and respiratory syncytial virus. Therefore, inducing type-I interferons while limiting CXCL13 levels overtime can be useful in such viral infections to stimulate antiviral response while preventing lung tissue damage due to excessive inflammation, particularly infection by SARS-COV2, influenza virus or respiratory syncytial virus. This increase in type-I interferon while simultaneously decreasing CXCL13 is a surprising effect of the probiotic compositions provided herein, since CXCL13 is known to be induced by type-I interferons. Remarkably, this reduction in CXCL13 did not compromise the activity of B-cells, as shown by the increased levels of immunoglobulins IgG and IgM shown in Example 2. Further, these results correlate with a minor duration of the clinical symptoms and with viral clearance as shown in Example 3.

Example 4 shows that *L. plantarum* CECT 30292 significantly overexpresses Plantaricin G (plnG) gene in comparison to the strain type WCFS1 and also in comparison to all other tested strains. Plantaricin G is a bacterial surface protein found in some strains of the *Lactobacillus plantarum* species. This protein is specifically implicated in mechanisms to inhibit the growth of competing pathogens. Importantly, among proteins generally produced by *L. plantarum*, plnG is particularly recognized by Antigen-Presenting Cells (APCs), i.e., immune cells in charge of searching for potential pathogens. APCs release interferons and other immunoregulatory signals upon activation, thus helping activate other immune cells such as antibody-producing B-cells and natural killer (NK)-cells.

As discussed above with respect to the webpage disclosure in clinicaltrials.gov, the statements in this webpage disclosure may be seen as mere statements that are not supported by any significant verifiable experimental data—it is evident that based on this webpage disclosure it was not plausible/credible that herein relevant positive effects may be obtained in human patients.

Based on the knowledge of the prior art, the skilled person could not have foreseen with a reasonable expectation of success the herein experimentally described significant positive effects. Of note, the clinical results have exceeded the expectations beyond the initial study design hypothesis. Thus, the herein experimentally described significant positive effects are unexpected for the skilled person and may be considered as a great contribution to the art.

Accordingly, an aspect of the invention relates to a probiotic composition comprising: *Lactobacillus plantarum* strain deposited under the Budapest Treaty in the Spanish Type Culture Collection (CECT) under accession number CECT 30292, or a bacterial strain derived thereof, *Lactobacillus plantarum* strain deposited under the Budapest Treaty in CECT under accession number CECT 7484, or a bacterial strain derived thereof, *Lactobacillus plantarum* strain deposited under the Budapest Treaty in CECT under accession number CECT 7485, or a bacterial strain derived thereof, and *Pediococcus acidilactici* strain deposited under the Budapest Treaty in CECT under accession number CECT 7483 or a bacterial strain derived thereof, wherein each derived bacterial strain:

(a) has a genome at least 99.90% identical to the genome of the correspondent deposited strain; and (b) retains at least one ability of the correspondent deposited strain, the abilities being selected from the group consisting of:

to increase remission of COVID-19;

to reduce the duration of symptoms of COVID-19;

to reduce SARSCoV-2 viral load;

to stimulate antibodies production against SARSCoV-2 virus (i.e., to increase of antibody levels);

to improve blood oxygen saturation; and to reduce the duration of low oxygen saturation in blood (i.e., hypoxemia).

Another aspect relates to *Lactobacillus plantarum* strain deposited under the Budapest Treaty in the Spanish Type Culture Collection (CECT) under accession number CECT 30292, or a bacterial strain derived thereof, wherein the derived bacterial strain:

(a) has a genome at least 99.90% identical to the genome of the correspondent deposited strain; and (b) retains at least one ability of the correspondent deposited strain, the abilities being selected from the group consisting of:

to increase remission of COVID-19;

to reduce the duration of symptoms of COVID-19;

to reduce SARSCoV-2 viral load;

to stimulate antibodies production against SARSCoV-2 virus (i.e., to increase of antibody levels);

to improve blood oxygen saturation; and to reduce the duration of low oxygen saturation in blood (i.e., hypoxemia).

The invention also relates to a probiotic composition comprising *Lactobacillus plantarum* strain CECT 30292 or a bacterial strain derived thereof with the above-mentioned characteristics.

Another aspect relates to a probiotic composition comprising *Lactobacillus plantarum* strain deposited under the Budapest Treaty in the Spanish Type Culture Collection (CECT) under accession number CECT 30292, or a bacterial strain derived thereof, wherein the derived bacterial strain:

(a) has a genome at least 99.90% identical to the genome of the correspondent deposited strain; and (b) retains at least one ability of the correspondent deposited strain in comparison with a control, the abilities being selected from the group consisting of:

to stimulate IgG and IgM antibodies production against SARSCoV-2 virus; particularly IgG antibody levels are at least doubled;

to increase interferon-beta levels, particularly interferon-beta levels are at least 20% increased;

to reduce CXCL13 levels;

has at least the copy number of plnG gene of the deposited strain; and to overexpress plantaricin G, particularly plantaricin G is at least four-fold overexpressed.

Another aspect relates to *Lactobacillus plantarum* strain deposited under the Budapest Treaty in the Spanish Type Culture Collection (CECT) under accession number CECT 30292.

Another aspect relates to a method for obtaining a mutant strain of *Lactobacillus plantarum* strain deposited under CECT 30292, comprising the following steps:

(i): making mutants of *L. plantarum* CECT 30292;

(ii): analyzing the in step (i) obtained mutants and identifying a mutant strain that retains or improves at least one ability of the deposited strain; and (iii) isolating the in step (ii) identified mutant strain to thereby obtain the mutant strain of *L. plantarum* CECT 30292, wherein the mutant strain retains or improves at least one ability of the deposited strain.

"Probiotic composition" and "probiotic compositions" are used herein to refer to the different compositions according to the different aspects and embodiments of the present invention.

The probiotic compositions described herein can be used for different medical applications/uses which are described herein in detail. All the uses described herein can be alternatively formulated as the use of any of the compositions described herein for the manufacture of a pharmaceutical product, a veterinary product, a medicament, an edible product, a food supplement, or a dietary product, for the prevention and/or treatment of the diseases disclosed herein.

This may be also alternatively formulated as methods of treating or preventing the diseases described herein or symptoms and/or complications thereof in a subject in need thereof comprising administering to the subject the herein described probiotic compositions.

An aspect of the invention relates to the probiotic composition for use as a medicament (i.e., for use in the treatment or prevention of a disease). This aspect can alternatively be formulated as a method for probiotic treatment, comprising administering in a need thereof an effective amount of a probiotic composition of the present invention. The term "probiotic" as used herein, refers to live microorganisms that, when administered in adequate amounts, confer a health benefit on the host.

An aspect of the invention relates to the probiotic composition according to the invention, for use in a method of treating, preventing, or ameliorating COVID-19 or symptoms, complications and/or sequela thereof. This aspect can alternatively be formulated as a method of treating, preventing, or ameliorating COVID-19 or symptoms and/or complications thereof in a subject in need thereof comprising administering to the subject the probiotic composition described herein.

Another aspect relates to the probiotic composition according to the invention, for use in a method of treating, preventing, or ameliorating an infectious disease or symptoms, complications and/or sequela thereof. This aspect can alternatively be formulated as a method of treating, preventing, or ameliorating an infectious disease or symptoms and/or complications thereof in a subject in need thereof comprising administering to the subject the probiotic composition described herein.

Another aspect relates to the probiotic composition according to the invention, for use in enhancing immune response (i.e., for use in promoting, stimulating or boosting immune response or immunity). This aspect can alternatively be formulated as a method of enhancing immune response in a subject in need thereof comprising administering to the subject the probiotic composition described herein.

Another aspect relates to a dietary supplement comprising the probiotic composition described herein and at least one acceptable excipient.

Another aspect relates to a pharmaceutical composition comprising an effective amount the probiotic composition described herein and at least one pharmaceutically acceptable excipient.

Another aspect relates to an edible product comprising the probiotic composition described herein and at least one edible ingredient.

Terms used in the claims and aspects of the invention are understood in its widely and common meaning in this description. Nevertheless, some are defined hereinafter in the detailed description of the invention.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein. The following examples and drawings are provided herein for illustrative purposes, and without intending to be limiting to the present invention.

DETAILED DESCRIPTION OF THE INVENTION

Definitions

Figure 1:
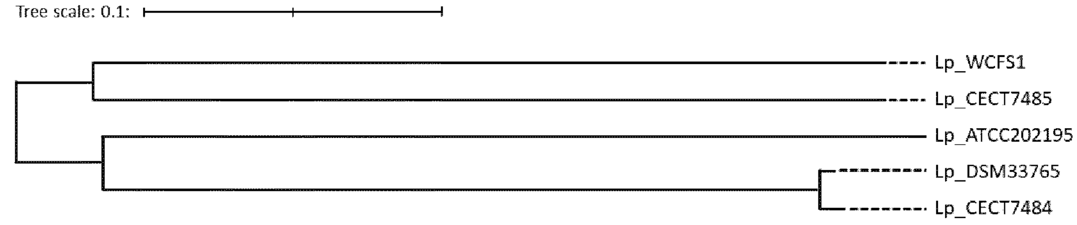
FIG. 1 shows a tree analysis based on ANI (Average Nucleotide Identity) where the train of *L. plantarum* DSM 33765 belongs to the same clade as CECT 7484 (ANI of 99.71%), while being more distantly related to reference strain WCFS1, as well as ATCC 202195 and CECT 7485 (ANI values of 98.7-98.8%). See working Example herein for further details.
Figure 2:
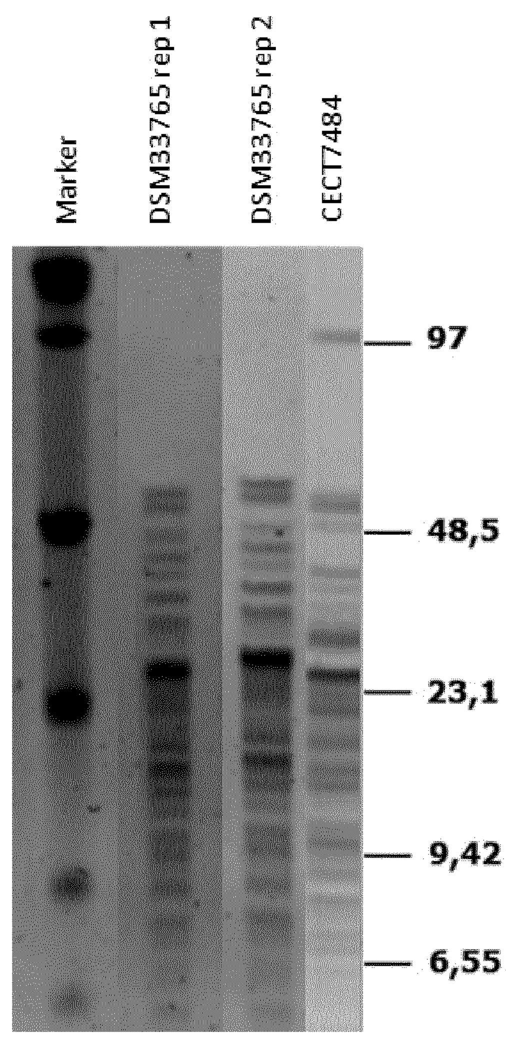
FIG. 2 shows a Pulse-field gel electrophoresis (PFGE), showing that the *L. plantarum* DSM 33765 strain (two replicated rep1 and rep2) has a reproducible PFGE profile, which is different than the profile of closely related strain *L. plantarum* CECT 7484. Particularly, compared to CECT 7484, strain DSM 33765 lacks a band of 97 kDa but has additional bands between 48.5 and 32.1 kDa. Hence, albeit closely related, both strains are demonstrated to be different one another. See working Example herein for further details.

Derived from: The terms "derived from," "derivative", "variant", "mutant" (e.g., "mutant strain"), or any grammatical variant thereof, as used herein, refer to a component that is isolated from or made using a specified molecule/substance (e.g., a strain of the present disclosure). For example, a bacterial strain that is derived from a first bacterial strain (e.g., a deposited strain) can be a strain that is identical or substantially similar to the first strain. In the case of bacterial strains, the derived strain can be obtained by, for example, naturally occurring mutagenesis, artificially-directed mutagenesis or artificially random mutagenesis.

Excipient: The terms "excipient" and "carrier" are used interchangeably and refer to an inert substance added to a e.g., pharmaceutical composition to further facilitate administration of a compound, e.g., a bacterial strain of the present disclosure.

Identity: As used herein, the term "identity" refers to the overall conservation of the monomeric sequence between polymeric molecules, e.g., between DNA molecules and/or RNA molecules. The term "identical" without any additional qualifiers, implies the sequences are 100% identical (100% sequence identity). Describing two sequences as, e.g., "70% identical," is equivalent to describing them as having, e.g., "70% sequence identity."

Calculation of the percent identity of two polymeric molecules, e.g., polynucleotide sequences, can be performed, e.g., by aligning the two sequences for optimal comparison purposes (e.g., gaps can be introduced in one or both of a first and a second polynucleotide sequences for optimal alignment). In certain aspects, the length of a sequence aligned for comparison purposes is at least about 30%, at least about 40%, at least about 50%, at least about 60%, at least about 70%, at least about 80%, at least about 90% or about 100% of the length of the reference sequence. The bases at corresponding base positions, in the case of polynucleotides, are then compared.

The percent identity between the two sequences is a function of the number of identical positions shared by the sequences, taking into account the number of gaps, and the length of each gap, which can be determined using a mathematical algorithm. Suitable software programs are available for alignment of both protein and nucleotide sequences. One suitable program to determine percent sequence identity is bl2seq, which performs a comparison between two sequences using either the BLASTN (used to compare nucleic acid sequences) or BLASTP (used to compare amino acid sequences) algorithm. Other suitable programs are, e.g., Needle, Stretcher, Water, or Matcher, part of the EMBOSS suite of bioinformatics programs. Sequence alignments can be conducted using methods known in the art such as MAFFT, Clustal (ClustalW, Clustal X or Clustal Omega), MUSCLE, MAUVE, MUMMER, RAST, etc.

In certain aspects, the percentage identity (% ID) of a first sequence to a second sequence is calculated as % ID=100×(Y/Z), where Y is the number of amino acid residues or nucleobases scored as identical matches in the alignment of the first and second sequences (e.g., as aligned by visual inspection or a particular sequence alignment program) and Z is the total number of residues in the second sequence. When comparing complete or near complete genomic nucleobase sequences, % ID is sometimes referred to as ANI (Average Nucleotide Identity).

Prevent: The terms "prevent," "preventing," "prophylaxis" and variants thereof as used herein, refer, e.g., to (i) partially or completely delaying onset of a disease, disorder and/or condition disclosed herein;
(ii) partially or completely delaying onset of one or more symptoms, features, or clinical manifestations, complications, or sequelae of a particular disease, disorder, and/or condition disclosed herein;
(iii) partially or completely delaying onset of one or more symptoms, features, or manifestations, complications, or sequelae of a particular disease, disorder, and/or condition disclosed herein;
(iv) partially or completely delaying progression from a particular disease, disorder and/or condition disclosed herein; and/or
(v) decreasing the risk of developing pathology associated with the disease, disorder, and/or condition disclosed herein.

Subject: The terms "subject," "patient," "individual," and "host," and variants thereof are used interchangeably herein and refer to any mammalian subject, particularly humans, but also including without limitation, humans, domestic animals (e.g., dogs, cats and the like), farm animals (e.g., cows, sheep, pigs, horses and the like), and laboratory animals (e.g., monkey, rats, mice, rabbits, guinea pigs and the like) for whom diagnosis, treatment, or therapy is desired. The methods described herein are applicable to both human therapy and veterinary applications.

Subject in need thereof: As used herein, "subject in need thereof includes subjects, such as mammalian subjects, that would benefit from administration of the compositions of the disclosure.

Therapeutically effective amount: As used herein the term "therapeutically effective amount" is the amount of a composition of the present disclosure that is sufficient to a produce a desired therapeutic effect, pharmacologic and/or physiologic effect on a subject in need thereof.

Treatment: The terms "treat," "treatment," "therapy," as used herein refer to, e.g., the reduction in severity of disease or condition disclosed herein; the amelioration or elimination of one or more symptoms, complication, or sequelae associated with a disease disclosed herein (e.g., a coronavirus disease such as COVID-19); the provision of beneficial effects to a subject with a condition/disease disclosed herein, without necessarily curing the disease or condition. The term also includes prophylaxis or prevention of a disease or condition or symptoms, complications, or sequelae thereof.

The term refers to a clinical or nutritional intervention to prevent the disease or condition; cure the disease or condition; delay onset of the disease or condition; delay onset of a symptom, complication or sequela; reduce the seriousness of the disease or condition; reduce the seriousness of a symptom, complication, or sequela; improve one or more symptoms; improve one or more complications; improve one or more sequelae; prevent one or more symptoms; prevent one or more complications; prevent one or more sequelae; delay one or more symptoms; delay one or more symptoms; delay one or more complications; delay one or more sequelae; ameliorate one or more symptoms; ameliorate one or more complications; ameliorate one or more sequelae; shorten the duration one or more symptoms; shorten the duration one or more complications; shorten the duration of one or more sequelae; reduce the frequency of one or more symptoms; reduce the frequency of one or more complications; reduce the frequency of one or more sequelae; reduce the severity of one or more symptoms; reduce the severity of one or more complications; reduce the severity of one or more sequelae; improve the quality of life; increase survival; prevent a recurrence of the disease or condition; delay a recurrence of the disease or condition; or any combination thereof, e.g., with respect to what is expected in the absence of the treatment with the composition of the present disclosure.

Symptom: As used herein, the term "symptom" refers to subjective or physical sign, indication, or evidence of disease or physical disturbance observed by the subject. In general, the term refers to any morbid phenomenon or departure from the normal in structure, function, or sensation, experienced by the patient and indicative of disease. Symptoms are felt or noticed by the individual experiencing the symptom but may not easily be noticed by others. In some aspects, a symptom can be a mild symptom, a moderate symptom, or severe symptom. As used herein, the term "mild symptom" refers to a symptom that is not life threatening and does not require, e.g., intensive care treatment (e.g., at a hospital ICU). As used herein, the term "moderate symptom" refers to a symptom that requires monitoring because it may become life threatening and may require, e.g., hospitalization. As used herein, the term "severe symptom" refers to a symptom that is life threatening and requires, e.g., intensive care treatment (e.g., at a hospital ICU).

Complication: As used herein, the term "complication" refers to a pathological process or event occurring during a disease or condition that is not an essential part of the disease or condition, where it may result from the disease/condition or from independent causes. Accordingly, the term complication refers to medical/clinical problems that are observed in subjects diagnosed with a disease or conditions disclosed herein, e.g., COVID-19. In some aspects, a complication can be temporary.

In some aspects, a complication can be chronic or permanent. As used herein, the term "sequela" refers to a long term, chronic, or permanent complication.

Probiotic Composition

As previously discussed, an aspect of the invention relates to a probiotic composition comprising *Lactobacillus plantarum* strain deposited under accession number CECT 30292, or a bacterial strain derived thereof.

In an embodiment, the *Lactobacillus plantarum* strain is the strain deposited under accession number CECT 30292.

In one embodiment, the probiotic composition further comprises, *Lactobacillus plantarum* CECT 7484, *Lactobacillus plantarum* CECT 7485, and *Pediococcus acidilactici* CECT 7483.

*Lactobacillus plantarum* CECT 30292 (also referred in this description as DSM 33765) was isolated from humans (fecal sample) and chicory (*Cichorium intybus*). The strain was deposited in the German Collection of Microorganisms and Cell Cultures GmbH (DSMZ) with address Leibniz-Institut DSMZ-Deutsche Sammlung von Mikroogranismen und ZellKulturen GmbH, Inhoffenstr, 7B D-38124 Braunschweig, Germany) The deposited strain received the accession number DSM 33765 and deposit date Jan. 27, 2021 (27.01.2021). The strain was also deposited in the Spanish Type Culture Collection (CECT, Parc Cientific de la Universitat de Valencia, Carrer del Catedratic Agustin Escardino Benlloch, 9, 46980 Paterna, Valencia, Spain) on Jan. 26, 2021 (26.01.2021) with accession number CECT 30292. Both deposits were performed under the conditions of the Budapest Treaty, are viable and keep all their features related to their deposit. They were deposited by the same applicant.

A particular embodiment is related to a *Lactobacillus plantarum* strain deposited under the Budapest Treaty in the Spanish Type Culture Collection (CECT) under accession number CECT 30292. The invention also relates to a probiotic composition comprising the *Lactobacillus plantarum* strain CECT 30292.

Strains *Lactobacillus plantarum* strains CECT 7485 and CECT 7484 and *Pediococcus acidilactici* strain CECT 7483 are described and protected in WO2011092261A1, whose content is incorporated herein by reference in its entirety. These three strains were deposited in the Spanish Type Culture Collection (Parc Cientific de la Universitat de Valencia, Carrer del Catedratic Agustin Escardino Benlloch, 9, 46980 Paterna, Valencia, Spain) on Feb. 4, 2009 (04.02.2009) by the same applicant of the present application.

As understood by the skilled person in the present context, a bacterial strain has been isolated from its natural environment, i.e., it is not present in its natural environment, so it is free from other organisms and substances present in the natural environment.

*Lactoplantibacillus plantarum* (*L. plantarum*) was previously known as *Lactobacillus plantarum*—thus, *Lactoplan-*

*tibacillus plantarum* and *Lactobacillus plantarum* are used indistinctly in this description.

A wide variety of lactic acid bacterial species have a long history of apparent safe use. The European Food Safety Authority has developed a system granting the "Qualified Presumption of Safety" (QPS) status to taxonomical units with a proven long history of apparent safe use. Strains *P. acidi-lactici* CECT 7483, *L. plantarum* CECT 7484 and *L. plantarum* CECT 7485 and *L. plantarum* DSM 33765 belong to bacterial species that have QPS status.

The emergence and spread of resistance to antimicrobials in bacteria pose a threat to human and animal health and present a major financial and societal cost. It has been found by whole genome sequence analysis that novel strain *L. plantarum* DSM 33765 does not possess antibiotic resistance genes. Strains CECT 7483, CECT 7484 and CECT 7485 do not possess antibiotic resistances either. Overall, these results preclude the risk of a potential transfer of antibiotic resistance to pathogenic species.

It is clear that by using the deposited strains as starting material, the skilled person in the art can routinely, by conventional mutagenesis or re-isolation techniques (i.e., reculturing), obtain further variants or mutants thereof that retain or enhance the herein described relevant features and advantages of the strains forming the composition of the invention. Thus, the invention also relates to variants of strains disclosed herein. As used herein, the term "variant" or "mutant" of a strain refers to any naturally-occurring or specifically developed strain obtained from the deposited reference strain, mainly by mutation, that retains at least one ability mentioned above of the deposited strain.

Example 5 shows the variability between the genomes of two different batches of the same strain (DSM 33765). It is proved that two isolates of the same strain can differ by 0.01% of average nucleotide identity (ANI). Therefore, a strain displaying 99.99% ANI to the genome of the correspondent deposited strain is considered the same deposited strain CECT 30292.

In a particular embodiment, the bacterial strain derived from the deposited strain has a genome at least 99.90% identical to the genome of the correspondent deposited strain; more particularly, % of identity is 99.91%, 99.92%, 99.93%, 99.94%, 99.95%, 99.96%, 99.97%, 99.98%, or 99.99%. Particularly the % of identity is at least 99.95%. In a particular embodiment, the mutants are obtained by using recombinant DNA technology. In another embodiment, the mutants are obtained by random mutagenesis. In another embodiment, the mutant is a naturally occurring variant. In another embodiment, the mutant is obtained by reculturing the deposited strain. Thus, another aspect of the invention relates to a method to obtain a strain derived from the deposited strain (in particular, *L. plantarum* CECT 30292), wherein the method comprises using the deposited strain as starting material and applying mutagenesis or reculturing, and wherein the obtained variant or mutant further retains or enhances at least one ability of the deposited strain.

This can alternatively be expressed as a method for obtaining a mutant strain of a deposited strain (in particular *L. plantarum* CECT 30292) comprising the following steps:

(i): making mutants of *L. plantarum* CECT 30292;

(ii): analyzing the in step (i) obtained mutants and identifying a mutant strain that retains or improves at least one ability of the deposited strain; and (111) isolating the in step (ii) identified mutant strain to thereby obtain the mutant strain of *L. plantarum* CECT 30292, wherein the mutant strain retains or improves at least one ability of the deposited strain.

In some embodiments, the obtained mutant retains (or improves) at least one ability of the correspondent deposited strain in comparison with a control, the abilities being selected from the group consisting of:

to increase remission of COVID-19;

to reduce the duration of symptoms of COVID-19;

to reduce SARSCoV-2 viral load;

to stimulate antibodies production against SARSCoV-2 virus; in particular to stimulate IgG and IgM antibodies production against SARSCoV-2 virus; more particularly IgG antibody levels are at least doubled;

to improve hypoxemia;

to reduce the duration of hypoxemia;

to increase interferon-beta levels, particularly interferon-beta levels are at least 20% increased;

to reduce CXCL13 levels;

has at least the copy number of plnG gene or more copies of the gene of the deposited strain; and to overexpress plantaricin G, particularly plantaricin G is at least four-fold overexpressed.

The control is understood as a placebo or a control strain which does not have such particular ability.

In a particular embodiment, the obtained mutant retains (or improves) at least one ability of the correspondent deposited strain, wherein the ability is selected from the group consisting of: to increase remission of COVID-19; to reduce the duration of symptoms of COVID-19; to reduce SARSCoV-2 viral load; to stimulate antibodies production against SARSCoV-2 virus; in particular to stimulate IgG and IgM antibodies production against SARSCoV-2 virus; more particularly IgG antibody levels are at least doubled; to improve hypoxemia; and to reduce the duration of hypoxemia. In a particular embodiment, the control for such abilities is a placebo.

In a particular embodiment, the obtained mutant retains (or improves) at least one ability of the correspondent deposited strain, wherein the ability is to stimulate antibodies production against SARSCoV-2 virus; in particular, to stimulate IgG and IgM antibodies production against SARSCoV-2 virus; more particularly IgG antibody levels are at least doubled. In a particular embodiment, the control for such ability is a placebo.

In a particular embodiment, the obtained mutant retains (or improves) at least one ability of the correspondent deposited strain, wherein the ability is to increase interferon-beta levels, particularly interferon-beta levels are at least 20% increased. In a particular embodiment, the control for such ability is a placebo.

In a particular embodiment, the obtained mutant retains (or improves) at least one ability of the correspondent deposited strain, wherein the ability is to reduce CXCL13 levels. In a particular embodiment, the control for such ability is a placebo.

In a particular embodiment, the obtained mutant retains (or improves) at least one ability of the correspondent deposited strain, wherein the ability is that has at least the copy number of plnG gene or more copies of the gene of the deposited strain. In a particular embodiment, the control for such ability is a strain which only has one copy of plnG gene, such as e.g., WCSF1 strain.

In a particular embodiment, the obtained mutant retains (or improves) at least one ability of the correspondent deposited strain, wherein the ability is to overexpress plantaricin G, particularly plantaricin G is at least four-fold overexpressed. In a particular embodiment, the control for such ability is e.g., WCSF1 strain.

The skilled person in the art will decide upon the adequate method to be employed for determining the abilities of the obtained mutant in respect of the correspondent deposited strain. Examples of possible methods to measure these abilities are shown in the Examples section.

Example 6 shows that the strain CECT 30292 has additional copies of the plnG gene in plasmids. Thus, a skilled in the art can attempt to increase the number of copies of plasmids containing the plnG gene, or to insert additional copies of the plnG gene into the bacterial DNA of the deposited strains. Therefore, in an embodiment, the bacterial strain derived thereof has been obtained derived from the deposited strain by insertion of additional copies of the plnG gene, either in the bacterial chromosome or in plasmids.

It is evident that it is routine work for the skilled person to obtain a mutant strain of CECT 30292 even without the knowledge of the genome sequence.

The strains forming part of the composition of the invention may be in the form of viable cells. Alternatively, the strain may be in the form of non-viable cells. This could include thermally killed micro-organisms or micro-organisms killed by exposure to altered pH, sonication, radiation or high pressure. Product preparation is simpler with non-viable cells, as cells may be incorporated easily into dietary, pharmaceuticals or edible products, and storage requirements are much less limited than viable cells.

The strains disclosed herein are produced by cultivating (or fermenting) the bacteria in a suitable artificial medium and under suitable conditions. By the expression, "artificial medium" for microorganisms is understood to be a medium containing natural substances, and optionally synthetic chemicals such as the polymer polyvinyl alcohol which can reproduce some of the functions of serums. Common suitable artificial media are nutrient broths that contain the elements including a carbon source (e.g., glucose), a nitrogen source (e.g., amino acids and proteins), water and salts needed for bacterial growth. Growth media can be liquid form or often mixed with agar or another gelling agent to obtain a solid medium. The strains can be cultivated alone to form a pure culture, or as a mixed culture together with other microorganisms, or by cultivating bacteria of different types separately and then combining them in the desired proportions. After cultivation, and depending on the final formulation, the strains may be used as purified bacteria, or alternatively, the bacterial culture or the cell suspension may be used, either as such or after an appropriate posttreatment. In this description, the term "biomass" is understood to be the bacterial strains culture obtained after cultivation (or fermentation as a term synonymous to cultivation).

In a particular embodiment, the strains are fermented in an artificial medium and submitted to a post-treatment after the fermentation, to obtain bacterial cells, and the resulting bacterial cells are in a liquid medium or in a solid form. Particularly, the post-treatment is selected from the group consisting of: drying, freezing, freeze-drying, fluid bed-drying, spray-drying and refrigerating in liquid medium, and more particularly, is freeze-drying.

By the term "post-treatment" is to be understood in the present context, any processing carried out on the biomass with the aim of obtaining storable bacterial cells. The objective of the posttreatment is decreasing the metabolic activity of the cells in the biomass, and thus, slowing the rate of cellular deleterious reactions. As a result of the post-treatment, the bacterial cells can be in solid or liquid form. In solid form, the stored bacterial cells can be a powder or granules. In any case, both the solid and liquid forms containing the bacterial cells are not present in nature, hence, are not naturally-occurring, since they are the result of artificial post-treatment process(es). The post-treatment processes may in particular embodiments require the use of one or more of so-called post-treatment agents. In the context of the present invention, the expression "post-treatment agent" refers to a compound used to perform the herein described post-treatment processes. Among the post-treatment agents are to be included, without limitation, dehydrating agents, bacteriostatic agents, cryoprotective agents (cryoprotectants), inert fillers (also known as lyoprotectants), carrier material (also known as core material), etc., used either alone or in combination.

There are two basic approaches to decrease the metabolic activity of the bacterial cells, and thus, two approaches to carry out the post-treatment. The first one is decreasing the rate of all chemical reactions, which can be done by lowering the temperature by refrigerating or freezing using refrigerators, mechanical freezers, and liquid nitrogen freezers. Alternatively, decreasing the rate of all chemical reactions can be achieved by adding substances that inhibit the growth of the bacterial cells, namely a bacteriostatic agent, abbreviated Bstatic.

The second approach to carry out the post-treatment is to remove water from the biomass, a process which can involve sublimation of water using a lyophilizer. Suitable techniques to remove water from the biomass are drying, freeze-drying, spray-drying or fluid bed-drying. Post-treatments that result in solid form may be drying, freezing, freeze-drying, fluid bed-drying, or spray-drying.

The post-treatment is particularly freeze-drying, which involves the removal of water from frozen bacterial suspensions by sublimation under reduced pressure. This process consists of three steps: pre-freezing the product to form a frozen structure, primary drying to remove most water, and secondary drying to remove bound water. Due to objective and expected variability of industrial processes for manufacturing and isolation of lyophilized bacterial cultures, the latter commonly contain a certain amount of inert filler also known as lyoprotectant. Its role is to standardize the content of live probiotic bacteria in the product. The following inert fillers in commercially available lyophilized cultures are used: sucrose, saccharose, lactose, trehalose, glucose, maltose, maltodextrin, corn starch, inulin, and other pharmaceutically acceptable non-hygroscopic fillers. Optionally, other stabilizing or freeze-protecting agents like ascorbic acid, are also used to form a viscous paste, which is submitted to freeze-drying. In any case, the so-obtained material can be grinded to appropriate size, including to a powder.

Alternatively to having biomass preserved in solid form, biomass may be also preserved in liquid form. This may be done by adding a bacteriostatic agent as described above to stop bacteria growth to the culture medium or with an intermediate step of harvesting cells, re-suspending the pellet in saline solution with a bacteriostatic agent, and optionally refrigerating it.

Sometimes, as described for instance above in the fluid bed-drying process, the probiotic preparation is subjected to an immobilization and/or coating, or encapsulation process in order to improve the shelf life and/or functionalities. Several techniques for immobilization, coating or encapsulation of bacteria are known in the art.

The effective amount of colony forming units (cfu) for each strain in the composition will be determined by the skilled in the art and will depend upon the final formulation. The term "colony forming unit" ("cfu") is defined as the number of bacterial cells as revealed by microbiological counts on agar plates.

In some embodiments, e.g., in edible products (e.g., yogurts, candies), the strain(s) are present in an amount from $10^5$ cfu/g to $10^{12}$ cfu/g, more particularly from $10^7$ cfu/g to $10^{11}$ cfu/g. In some embodiments, e.g., in dietary supplements (e.g., a tablet), the strain(s) are present in an amount ranging from $10^6$ and $10^{12}$ cfu per dose (e.g., a tablet), and particularly from $10^8$ and $10^{11}$ cfu per dose.

In a particular embodiment, the probiotic composition is comprised by 50% of the strain *L. plantarum* CECT 30292 (e.g., 1 billion cfu), and 50% of a mixture of *L. plantarum* CECT 7485, CECT 7484, and *P. acidilactici* CECT 7483 (e.g., the mixture having an equivalent proportion of the three strains and a total of 1 billion cfu).

As known by the skilled person, the effective amount of colony units can also be measured by the effective amount of active fluorescent units (afu). The term "active fluorescent unit" ("afu") is defined as the number of bacterial cells as revealed by flow cytometry counts in a gate specific for fluorescence characteristics of presumed live cells. Therefore, the skilled person would consider the above-mentioned specific quantities of colony forming units (cfu) to be about the same quantity of active fluorescence units (afu).

In one embodiment, the probiotic composition is a solid composition.

In another embodiment, the probiotic composition is a solid composition comprising: a freeze-dried bacterial biomass comprising from about $10^5$ cfu to about $10^{12}$ cfu of each strain; and a cryoprotectant.

Particularly, the probiotic composition comprises at least one cryoprotectant that is an allergen-free cryoprotectant.

In some embodiments, the probiotic composition comprises at least one cryoprotectant selected from the group consisting of: maltose, trehalose, mannitol (particularly, d-mannitol), saccharose, lectose, dextrose, sodium ascorbate or sodium citrate.

More particularly, the composition further comprises a pharmaceutically acceptable carrier chosen from an emulsion, a suspension, a gel, a paste, granules, a powder, and a gum. Particularly, the carrier is an allergen-free carrier.

In some embodiments, the probiotic composition comprises one or more carriers selected from the group consisting of: maltodextrin, cellulose, starches of various types, inulin, lactose, or carrier with 5 reduced water activity.

Medical Uses of the Probiotic Composition—Method of Treating, Preventing, or Ameliorating COVID-19 or Symptoms, Complications and/or Sequela Thereof In some embodiments, the administration of the probiotic composition results in the treatment, prevention or amelioration at least one symptom of COVID-19 selected from the group consisting of:—fever;

cough, particularly dry cough;
headache;
shortness of breath;
bodily pain, particularly muscle pain;
low oxygen saturation (hypoxemia) in blood, particularly an oxygen saturation SaO2 or SpO2<92%; and
diarrhea.

As known by the skilled person, SaO2 is an alternative measure of oxygen saturation in blood, that refers to oxygen saturation measured in arteries and the later to oxygen saturation measured by pulse oximetry. SaO2 measures equivalent to SpO2 measures can be used indistinctly in this description.

In some embodiments, the administration of the probiotic composition results in at least one outcome (i.e., effect) selected from the group consisting of:

remission of COVID-19;
reduction of the duration of symptoms of COVID-19;
reduction of SARS-CoV-2 viral load;
stimulation of antibodies production against SARS-CoV-2 virus (i.e., increase of antibody levels); particularly stimulation of IgG and IgM antibodies production against SARSCoV-2 virus; more particularly IgG antibody levels are at least doubled;
improvement of blood oxygen saturation (hypoxemia); and
reduction of the duration of low oxygen saturation in blood (i.e., hypoxemia).

In some embodiments, the administration of the probiotic composition results in at least one outcome (i.e., effect) selected from the group consisting of:

increase of interferon-beta levels, particularly interferon-beta levels are 20% increased; and
reduction of CXCL13 levels.

In some embodiments, the administration of the probiotic composition to the subject can avoid hospitalization or reduce hospitalization time, avoid ICU admission (i.e., eliminate the need for ICU treatment), delay the need for ICU treatment, reduce (shorten) ICU treatment time, reduce patient mortality rate, increase patient survival rate, reduce patient's chance of death, increase patient's chance of survival, decrease patient's risk of death, reduce the severity of at least one symptom, reduce the severity of at least one complication, reduce the severity of at least one sequela, reduce the duration of at least one symptom, reduce the duration of at least one complication, reduce the duration of at least one sequela, or any combination thereof. Accordingly, the present disclosure provides methods to avoid or reduce hospitalization, reduce (shorten) ICU treatment time, delay the need for ICU treatment, avoid ICU admission (i.e., eliminate the need for ICU treatment), reduce patient mortality rate, increase patient survival rate, reduce patient's chance of death, increase patient's chance of survival, decrease patient's risk of death, reduce the severity of at least one symptom, reduce the severity of at least one complication, reduce the severity of at least one sequela, reduce the duration of at least one symptom, reduce the duration of at least one complication, reduce the duration of at least one sequela, or any combination thereof, in a subject and comprises administering the probiotic composition to the subject.

Medical Uses of the Probiotic Composition—Method of Treating, Preventing, or Ameliorating an Infectious Disease or Symptoms, Complications and/or Sequela Thereof.

As discussed herein, the probiotic composition presents a high efficacy in inducing remission of COVID-19 patients, as well as shortening duration of symptoms (e.g., shortness of breath, hypoxemia, diarrhea) and increasing virus-specific antibodies. Moreover, the composition has shown a significant beneficial effect in reducing the duration of low oxygen saturation in blood (hypoxemia).

Accordingly, the experimental data herein provides evidence that it is plausible that the probiotic composition would have significant positive effects in other infectious diseases. Particularly, the probiotic composition would have significant positive effects in other infectious diseases characterized in presenting one or more of the above mentioned respiratory and/or gastrointestinal symptoms.

In particular, the experimental data herein provides evidence that it is plausible that the probiotic composition would have significant positive effects in treating other viral respiratory infections with shortness of breath and hypoxemia (particularly SpO2 below 92%), e.g., SARS, MERS, human adenovirus 55, influenza of type A, particularly H1N1, or novel emerging viruses.

Particularly, hypoxemia occurs in a respiratory infectious disease related to viral bronchiolitis infections of the lungs in infants and children. Viral bronchiolitis is most typically caused by Respiratory Syncytial Virus, but can also be caused by rhinovirus, adenovirus, pneumovirus, human bocavirus, influenza virus or parainfluenza virus. Simultaneous bronchiolitis by more than one virus in the same individual is often reported. Hypoxemia has also been identified as a risk factor for death from viral influenza. The probiotic composition described herein presents a high efficacy in reducing symptoms related to respiratory tract infections. In particular, the experimental data herein provides evidence that it is plausible that the probiotic composition would have significant positive effects in treating other respiratory infections (e.g., viral) producing shortness of breath or hypoxemia (particularly SaO2 or SpO2<92%), e.g., severe influenza or viral bronchiolitis. Particularly, the experimental data herein provides evidence that it is plausible that the probiotic composition would have significant positive effects in treating low oxygen saturation in blood (particularly SpO2 below 92%).

Accordingly, in some embodiments, the infectious disease is caused by a bacterial, a viral, a parasitic and/or a fungal infection.

In a particular embodiment, the infectious disease is caused by a viral infection. More particularly, the viral infection is selected from the group consisting of adenovirus, viral hepatitis (particularly hepatitis C virus), viral encephalitis (particularly herpes simplex encephalitis), human bocavirus, human rhinovirus, influenza virus, particularly influenza virus of type A (particularly H1N1 and its variants), parainfluenza virus, pneumovirus, coronavirus, particularly beta-coronaviruses (more particularly SARS-CoV1, SARS-CoV2 or MERS-CoV), respiratory syncytial virus, rhinovirus and novel or emerging viruses. More particularly, the viral infection is a coronavirus, influenza or respiratory syncytial viral infection.

In a particular embodiment, the viral infection is a coronavirus infection. Coronaviruses are large, enveloped, single-stranded RNA viruses found in humans and other mammals. Coronaviruses (CoV) induce acute and chronic diseases. Coronaviruses cause respiratory, gastrointestinal, and neurological disease. There are 7 known coronaviruses to cause disease in humans: On the one hand, 229E, OC43, NL63, and HKU1 typically produce common cold symptoms not easily separable from symptoms caused by other respiratory viruses, and with no shortness of breath and no complications in immunocompromised individuals. Thus, in some embodiments, the coronavirus is e.g., 229E, OC43, NL63, and HKU1 or mutants thereof.

On the other hand, SARS-CoV-1, MERS-CoV and SARS-CoV-2 (all three belonging to the betacoronavirus subgroup) can produce more severe disease, ranging from dyspnea (shortness of breath) and low blood oxygen saturation (hypoxemia) to death. In particular, SARS-CoV-2 is the third coronavirus that has caused severe disease in humans to spread globally in the past 2 decades. These three types of CoV are CoV-associated severe acute respiratory syndrome (SARS-CoV-1 and SARS-CoV-2) and the Middle East respiratory syndrome associated with CoV (MERS-CoV).

In a particular embodiment, the coronavirus is a beta-coronavirus.

In a particular embodiment, the coronavirus is SARS-CoV-2 virus, SARS-CoV-1 virus, or MERS-CoV virus.

In some embodiments, the viral infection is caused by the SARS (Severe Acute Respiratory Syndrome) virus or SARS-CoV-1, a virus identified in 2003. SARS was first reported in Asia in February 2003. The illness spread to more than two dozen countries in North America, South America, Europe, and Asia before the SARS global outbreak of 2003 was contained. Since 2004, there have not been any known cases of SARS reported anywhere in the world. In some aspects, the coronavirus infection is caused by the MERS (Middle East Respiratory Syndrome) virus or MERS-CoV. MERS is viral respiratory illness that is new to humans. It was first reported in Saudi Arabia in 2012 and has since spread to several other countries, including the United States. Most people infected with MERS-CoV developed severe respiratory illness, including fever, cough, and shortness of breath.

In some embodiments, the viral infection is caused by SARS-CoV-2. As used herein, the terms "SARS-CoV-2," "SARS-CoV-2 virus," and "COVID-19 virus" are used interchangeably to refer to the coronavirus causing COVID-19 (coronavirus disease 2019). As used herein, the term "COVID-19" refers to the viral infection caused SARS-CoV-2. COVID-19 is a new infectious disease caused by the severe acute respiratory syndrome 2 coronavirus (SARS-CoV-2). COVID-19 disease was described for first time on Dec. 1, 2019 and became pandemic in few weeks. Studies demonstrate that SARS-CoV-2 induces a cytokine storm that is associated with the severity of COVID-19 disease and its prognosis. COVID-19 patients can develop mild symptoms (local symptoms in the upper respiratory tract with fever, muscle pain, etc.), moderate (mild pneumonia) or severe, including severe pneumonia, acute respiratory distress syndrome (ARDS), sepsis and septic shock. Nevertheless, although most individuals infected with SARS-CoV-2 may not have any illness or can develop mild illness, SARS-CoV-2 infection is not simply a common cold.

In some embodiments, the viral infection can be caused by other viruses such as e.g.: human adenovirus 55, influenza virus (e.g., influenza of type A, particularly H1N1) or Respiratory syncytial Virus.

In one embodiment, the infectious disease results in (or induces) a respiratory disease.

In a particular embodiment, the respiratory disease is characterized by shortness of breath.

In a particular embodiment, the respiratory disease is characterized by hypoxemia (particularly SaO2 or SpO2 below 92%).

In a particular embodiment, the respiratory disease affects the upper respiratory tract.

In a particular embodiment, the respiratory disease affects the lower respiratory tract (i.e., lung, alveoli).

In a particular embodiment, the respiratory disease is pneumonia, particularly mild or severe pneumonia.

In a particular embodiment, the respiratory disease is ARDS.

As used herein the terms "Acute Respiratory Distress Syndrome" and "ARDS" refers to a disease or condition of the lungs in which an infection (e.g., a viral infection) or trauma to the lungs leads to inflammation of the lungs, accumulation of fluid in the alveolar air sacs, low blood oxygen, and respiratory distress. Accordingly, in some embodiments, the present disclosure provides a method to treat ARDS comprising administering a probiotic composition of the present disclosure.

ARDS is a life-threatening condition, and severe injury occurs to most or all of both lungs. ARDS is a rapid onset of progressive malfunction of the lungs, especially with regard to the ability to take in oxygen, usually associated with the malfunction of other organs. ARDS is characterized by diffuse pulmonary microvascular injury resulting in increased permeability and, thus, non-cardiogenic pulmonary edema. The basic abnormality in ARDS is the disruption of the normal alveolar-capillary barrier. Alternative terms frequently used to refer to ARDS include adult hyaline-membrane disease, adult respiratory insufficiency syndrome, congestive atelectasis, hemorrhagic lung syndrome, Da Nang lung, stiff-lung syndrome, shock lung, white lung and wet lung, among others.

In some embodiments, a patient is considered to suffer from "ARDS" if the following symptoms are present:

1) Clinical evidence of respiratory distress.
2) Chest radiograph revealing diffuse bilateral airspace disease ("pulmonary edema").
3) Hypoxemia that is difficult to correct with oxygen supplementation.
4) Hemodynamic evidence of a pulmonary artery occlusion (wedge) pressure <18 mm Hg.
5) Thoracic static compliance less than 40 mL/cm of water.

In some embodiments, the cause of ARDS is, e.g., severe, widespread infection (sepsis); severe low blood pressure (shock); pneumonia; aspiration (inhalation) of food into the lung; injury to the lungs from breathing high concentrations of oxygen; pulmonary embolism; chest injury; burns; overdose of a drug; or disseminated intravascular coagulation.

In some embodiments, sequelae resulting from lung edema in ARDS patients include a decrease in lung volumes, compliance, and large intrapulmonary shunts (blood perfusing unventilated seg-merits of the lung). The decrease in lung volume (residual volume) contributes to ventilation/perfusion inequality. The decrease in lung compliance is caused by the increased lung recoil pressure of the edematous lung, which clinically increases the work of breathing and leads to respiratory muscle fatigue. ARDS affects pulmonary vasculature. Pulmonary hypertension not related to hypoxemia is very common in patients with ARDS. Pulmonary hypertension is caused by a three-to-five fold increase in the pulmonary vascular resistance (PVR) and is associated with an increase in the right ventricular work.

Common symptoms of ARDS include dyspnea, tachypnea, dry cough, retrosternal discomfort, and agitation. In some aspects, the patient appears in moderate to severe respiratory distress and may have cyanosis. In some aspects, examination of the lungs reveals coarse crackles and bronchial breath sounds. In some aspects, the patient requires assisted mechanical ventilation.

SARS-CoV-2 can also have gastrointestinal affectations due to microinflammation, vascular damage and dysbiosis of the gastrointestinal tract. Consequently, between 9% to 34% of COVID-19 patients suffer from diarrhea. As discussed herein, the probiotic composition of the invention significantly shortens the duration of diarrhea in COVID-19 patients. The mean duration of diarrhea in patients receiving the probiotic composition was less than half than the mean duration of the placebo group. Accordingly, the experimental data herein provides evidence that it is plausible that the probiotic composition would have significant positive effects in the duration of gastrointestinal symptoms such as diarrhea caused by diseases and infections other than COVID-19.

Accordingly, in one embodiment, the infectious disease results in (i.e., induces) a gastrointestinal disease.

In one embodiment, the gastrointestinal disease is characterized by microinflammation, vascular damage and/or dysbiosis of the gastrointestinal tract.

In some embodiments, in relation to the infectious diseases and the resulting respiratory and/or gastrointestinal diseases, the administration of the probiotic composition results in the treatment, prevention or amelioration of at least one symptom selected from the group consisting of:—fever;

cough, particularly dry cough;
headache;
shortness of breath;
bodily pain, particularly muscle pain;
low oxygen saturation (hypoxemia) in blood, particularly an oxygen saturation SaO2 or SpO2<92%; and
diarrhea.

In some embodiments, the administration of the probiotic composition results in at least one outcome (i.e., effect) selected from the group consisting of:

remission of infectious disease;
reduction of the duration of symptoms;
reduction of viral load;
stimulation of antibodies production (i.e., increase of antibody levels);
particularly stimulation of IgG and IgM antibodies production; more particularly IgG antibody levels are at least doubled;
improvement of blood oxygen saturation (hypoxemia); and
reduction of the duration of low oxygen saturation in blood (i.e., hypoxemia).

In some embodiments, the administration of the probiotic composition results in at least one outcome (i.e., effect) selected from the group consisting of:

increase of interferon-beta levels, particularly interferon-beta levels are 20% increased; and —reduction of CXCL13 levels.

In some embodiments, the present disclosure provides a method to select a subject with a disease or condition disclosed herein (e.g., COVID-19) for treatment with the probiotic composition according to the invention, comprising determining whether a biomarker selected from the group consisting of lymphopenia, neutrophilia, activation of coagulation (as shown, e.g., by an increase in D-dimer values), acute kidney injury (as shown, e.g., by increased blood urea and creatinine), increased levels of IL-6, increase in cardiac troponin I in plasma, increase in lactate dehydrogenase in plasma, increase in ferritin in plasma, increased levels of IL-10, increased levels of TNFa, reduced levels of CD4+ T-cells, reduced levels of CD8+ T-cells, leukocytosis, increase in procalcitonin levels, decrease in expression of IFNy in CD4+ T-cells, increase in cytokine levels produced by highly inflammatory macrophages, or any combination is present, wherein the presence of the biomarker indicated that the subject can be treated with probiotic composition disclosed herein.

Medical Uses of the Probiotic Composition—Enhancing Immune Response

Protection against COVID-19 is mediated in large part by an immune response directed against the SARS-CoV-2 spike (S)-protein. The S-protein is responsible for virus-cell binding and is the target for virus-neutralizing antibodies. Functional neutralizing antibodies specific to SARS-CoV-2 that are produced following infection, vaccination, or both (anti-spike glycoprotein and anti-RBD) are considered important for viral neutralization and viral clearance and are quantified by use of in vitro neutralization assays. Therefore, potentiating the production of antibodies specific to SARS-CoV-2 is of great interest to achieve long-term immunity, derived both from an initial infection and/or a vaccine. Particularly, antibodies of the IgA type have been shown to dominate the immune response to SARS-CoV-2 during the early days of the infection, but rapidly wanes after the 3rd week of the infection, while antibodies of the IgG type markedly increase their positivity rate.

As discussed herein, the probiotic composition of the invention enhances the immune response of patients resulting in a significant increase in the concentration of antibodies of type IgG and IgM ($p<0.001$). Remarkably, at day 30 of intervention, subjects receiving the probiotic composition had IgG levels twice as high as those of subject in placebo group. Accordingly, the experimental data herein provides evidence that it is plausible that the probiotic composition would have significant positive effects in the stimulation of the immune response of patients, and particularly of the production of antibodies, derived both from an initial infection and/or a vaccine.

Furthermore, from the above-mentioned evidence it is plausible that the probiotic composition would also have significant positive effects in the stimulation of the immune response (e.g., increase the production of antibodies) derived from other infections (e.g., bacterial or viral infections) or vaccines, particularly in the case of viral infections and/or viral vaccines.

Accordingly, in some embodiments, the probiotic composition is used in enhancing, accelerating and prolonging the immune system response.

In a particular embodiment, the administration of the probiotic composition stimulates the production of antibodies (particularly IgG and/or IgM).

In one embodiment, the immune system response comprises the production of antibodies (particularly IgG and/or IgM), particularly IgG antibody levels are at least doubled.

In other embodiments, the probiotic composition is used as adjuvant, immunostimulant, immune potentiator, or immunomodulator.

In some embodiments, the probiotic composition disclosed herein can be administered in combination with other therapeutic and/or prophylactic treatments (e.g., anticoagulants, anti-inflammatories, or blood pressure regulators). The probiotic composition and the other treatment can be formulated for a separate, sequential, concomitant administration or in admixture.

In some embodiments, the probiotic composition is used concomitantly with other treatments used for respiratory infections, particularly respiratory infections of viral origin causing hypoxemia, particularly COVID-19, such as but not limited to corticosteroids (e.g., dexamethasone, prednisone, methylprednisolone, or hydrocortisone), antipyretics (e.g., acetaminophen or non-steroidal antiinflammatory drugs such as ibuprofen and similar compounds), virus-specific neutralizing antibodies (e.g., REGN-COV2), vaccines (e.g., RNA vaccines, vaccines using recombinant chimeric viruses or peptide vaccines), molecules with antiviral activity (e.g., interferon, plitidepsin, remdesivir, oseltamivir and similar compounds) or blocking cytokine signaling (e.g. tocilizumab).

In some embodiments, the probiotic composition is administered in combination with a vaccine. In an embodiment, the probiotic composition is for the concomitant use in combination with a vaccine.

In some embodiments, the probiotic composition is administered in combination with an antiinflammatory drug, e.g., an anti-inflammatory corticosteroid. Examples of corticosteroid are methylprednisolone, fludrocortisone, hydrocortisone, prednisone, prednisolone, flunisolide, fluticasone, beclomethasone, budesonide, ciclesonide, mometasone, and any combination thereof. In an embodiment, the probiotic composition is for the concomitant use in combination with an antiinflammatory drug.

In one embodiment, the probiotic composition is administered in combination with an antipyretic drug.

Products Comprising the Probiotic Compositions

In some embodiments, the bacterial strains described herein can be formulated for a separate, sequential, concomitant administration or in admixture. The administration regimens and forms will be determined by the skilled in the art. Administration of the bacterial strains can be administered separately (waiting a time interval between the administration of a first bacteria strain and a second bacteria strain), sequentially (one after the other), concomitantly (simultaneously) or in admixture (together). Therefore, they can be administered as separate forms or as a part of a single composition. When the products are administered in separate dosage forms, the dosage forms can be in the same or different containers or e.g., capsules or pills. In a particular embodiment, the strains described herein are administered in a single composition, e.g., a tablet.

The probiotic compositions described herein can be formulated as edible, pharmaceutical or veterinary products, in which the strains are the only active agents or are mixed with one or more other active agents and/or are mixed with pharmaceutically or veterinary acceptable excipients (in the case of a pharmaceutical or veterinary product) or adequate additives (in the case of an edible product). Preferably, the additional active agent or agents are other probiotic bacteria which are not antagonistic to the strains forming the composition of the invention. Depending on the formulation, the strains may be added as purified bacteria, as a bacterial culture, as part of a bacterial culture, as a bacterial culture which has been post-treated, and alone or together with suitable carriers or ingredients. Prebiotics such as fructooligosaccharides (particularly inulins), galactooligosaccharides, xylo-oligosaccharides, arabinoxylan-oligosaccharides, pectins, beta-glucans or partially hydrolyzed guar gum can be added also.

In some embodiments, the probiotic composition is in the form of a pharmaceutical composition comprising an effective amount of the probiotic composition and at least one pharmaceutically acceptable excipient.

In particular embodiments, the compositions of the invention are formulated as pharmaceutical products, particularly, as food supplements. The term "pharmaceutical product" is understood in its widest meaning in this description, including any composition that comprises an active ingredient, in this case, the strains described herein particularly in form of composition together with pharmaceutically acceptable excipients. This term is not limited to medicaments.

The term "pharmaceutically acceptable" is art-recognized, and includes compounds, materials, compositions, carriers, vehicles and/or dosage forms which are, within the scope of sound medical judgment, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts. Some non-limiting examples of materials which may serve as pharmaceutically acceptable carriers include: sugars, such as lactose, glucose and sucrose; starches, such as corn starch and potato starch;

cellulose, and its derivatives, such as sodium carboxymethyl cellulose, ethyl cellulose and cellulose acetate; powdered tragacanth; malt; gelatin; talc; cocoa butter and suppository waxes; oils, such as peanut oil, cottonseed oil, sunflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Excipients are selected, without limitation, from the group comprising: fillers/diluents/bulking agents, binders, antiadherents, disintegrants, coatings, anti-caking agents, antioxidants, lubricants, sweeteners, flavors, colors, tensides and other classes of pharmaceutically and veterinary acceptable excipients.

Fillers are selected, without limitation, from the group comprising: inulin, oligofructose, pec-tin, modified pectins, microcrystalline cellulose, lactose, starch, maltodextrin, saccharose, glucose, fructose, mannitol, xylitol, non-crystallizing sorbitol, calcium carbonate, dicalcium phosphate, other inert inorganic and organic pharmacologically acceptable fillers, and mixtures of these substances. At dosage form of oral suspension, fillers or diluents are selected from the group comprising: vegetable oil, oleic acid, oleyl alcohol, liquid polyethylene glycol, other pharmacologically acceptable inert liquids, or mixtures of these substances.

Binders are used in solid dosage forms, e.g., to hold the ingredients in a tablet together, to ensure that tablets and granules can be formed with required mechanical strength, and to give volume to low active dose tablets. Binders in solid dosage forms like tablets are: lactose, sucrose, corn (maize) starch, modified starches, microcrystalline cellulose, modified cellulose (e.g., hydroxypropylmethylcellulose (HPMC) and hydroxyethylcellulose), other water-soluble cellulose ethers, polyvinylpyrrolidone (PVP) also known as povidone, poly-ethylene glycol, sorbitol, maltitol, xylitol and dibasic calcium phosphate; other suitable pharmacologically acceptable binders, or mixtures of these substances.

Antiadherents are used to reduce the adhesion between the powder (granules) and the punch faces and thus prevent sticking to tablet punches. They are also used to help protect tablets from sticking. The most commonly used is magnesium stearate.

As disintegrants and superdisintegrants in solid dosage forms like tablets and capsules, the following substances, without limitation, are used: cross-linked polyvinylpyrrolidone, sodium starch glycolate, sodium carboxymethyl cellulose, calcium carboxymethyl cellulose, and formaldehyde-casein, other suitable pharmacologically acceptable disintegrant and superdisintegrant, or their mixtures.

Coatings in the case of solid dosage forms, such as tablets and granules for capsule filling, protect the ingredients from deterioration by moisture in the air, make large, unpleasant-tasting tablets easier to swallow and/or in the case of enteric coatings ensure intact passage through a strong acidic medium of gastric juice (pH around 1), and which allow release in duodenum or ileum (small intestine). For most coated tablets, a cellulose ether hydroxypropyl methylcellulose (HPMC) film coating is used. Occasionally, other coating materials are used, e.g., synthetic polymers and co-polymers like polyvinylacetate phthalate (PVAP); co-polymers of methyl acrylate-metacrylic acid; copolymers of methyl metacrylate-metacrylic acid; shellac, corn protein zein or other polysaccharides; waxes or wax-like substances such as beeswax, stearic acid; higher fatty alcohols like cetyl or stearyl alcohol; solid paraffin; glycerol monostearate; glycerol distearate, or their combinations. Capsules are coated with gelatin or hydroxypropyl methylcellulose.

Enteric coatings control the rate of drug release and determine where the drug will be released in the digestive tract. Materials used for enteric coatings include fatty acids, waxes, shellac, plastics, and plant fibers and their mixtures, also in combination with other above-mentioned coatings.

An anticaking agent is an additive placed in powdered or granulated materials to prevent the formation of lumps (caking) and for easing packaging, transport, and consumption. As anti-caking agents in solid dosage forms like tablets, capsules, or powders, the following are used: magnesium stearate, colloidal silicon dioxide, talc, other pharmacologically acceptable anticaking agents, or their mixtures.

Lubricants are used in solid dosage forms, in particular in tablets and capsules, to prevent ingredients from clumping together and from sticking to the tablet punches or capsule filling machine, and also in hard capsules. As lubricants talc or silica, and fats, e.g., vegetable stearin, magnesium stearate or stearic acid, and mixtures thereof, are the most frequently used lubricants in tablets or hard gelatin capsules.

Sweeteners are added to make the ingredients more palatable, especially in solid dosage forms, e.g., chewable tablets, as well as in liquids dosage forms, like cough syrup. Sweeteners may be selected from artificial, natural or synthetic or semi-synthetic sweeteners; non-limiting examples of sweeteners are aspartame, acesulfame potassium, cyclamate, sucralose, saccharine, sugars or any mixture thereof, Flavors can be used to mask unpleasant tasting active ingredients in any dosage form. Flavorings may be natural (e.g., fruit extract) or artificial. For example, to improve: (1) a bitter product, mint, cherry or anise may be used; (2) a salty product, peach or apricot or liquorice may be used; (3) a sour product, raspberry; and (4) an excessively sweet product, vanilla.

Except auxiliary substances from the class of excipients, the formulation from the present invention can contain other pharmacologically active or nutritive substances including, but not limited, to vitamins, such as vitamin D (calciferol) in the pharmaceutically acceptable chemical form, salt or derivatives; minerals in the form of pharmaceutically and nutritive acceptable chemical form; and L-amino acids. Regarding the preparation of the formulations of the present invention, it is within the scope of ordinary person skilled in the art and will depend upon the final dosage formulation. For instance, and without limitation, when the final dosage form is an oral solid one, such as tablets, capsules, powder, granules, oral suspension, etc. the process for preparation of solid dosage forms of the formulation includes homogenization of: (1) the active ingredient(s), comprising at least one or more post-treated probiotic bacteria of the invention in an effective amount; (2) with one or more excipients to form homogeneous mixture which is, e.g., according to requirements, subjected to lubrication with magnesium stearate or other lubricants yielding final dosage form of powder. Such homogeneous powder is filled into ordinary gelatin capsules or, alternatively, into gastro-resistant capsules. In the case of tablets, they are manufactured by direct compression or granulation. In the first case, a homogeneous mixture of active ingredients and suitable excipients such as anhydrous lactose, non-crystallizing sorbitol, and others is prepared. In the second case, tablets are processed of the mixture in granulated form. Granules are prepared by granulation process of active ingredients of the formulation with suitable fillers, binders, disintegrants, and small amount of purified water. Such pre-pared granules are sieved and dried until the water content of <1% w/w.

Regarding the process for preparation of liquid dosage forms (e.g., oral suspension), it involves homogenization of the active ingredient(s) of the formulation comprising at least one or more posttreated probiotic bacteria of the invention in an effective amount in an inert liquid diluent (filler) such as various vegetable oils like sunflower, soybean or olive oil; oleic acid; oleyl alcohol; liquid polyethylene glycols like PEG 200, PEG 400 or PEG 600; or other inert pharmacologically acceptable liquids. The process further involves treatment of homogeneous mixture with one or more processes selected from the group comprising: (1) stabilization of the formulation, by addition and homogenization of suspension stabilizers like beeswax, colloidal silicon dioxide, etc.; (2) sweetening of the formulation, by addition and homogenization of sweetener; (3) flavoring of the formulation, by addition and homogenization of flavoring. Such forms of the formulation can contain also other excipients or ingredients usually employed in the art.

The pharmaceutical product can adopt different forms or names depending on the product approval route and also depending on the country. For instance, a medicament is a particular pharmaceutical product. A medical food is another particular pharmaceutical product. The terms "medical food" or "food for special medical purposes" are used in some countries to refer to a food specially formulated and intended for the dietary management of a disease that has distinctive nutritional needs that cannot be met by normal diet alone. They are defined in regulations such as the Food and Drug Administration's 1988 Orphan Drug Act Amendments in the United States, and the Commission Directive 1999/21/EC in Europe. Medical foods are distinct from the broader category of food supplements and from traditional foods that bear a health claim. Thus, in a particular embodiment, the strains of the invention are formulated as a medical food.

In some embodiments, the probiotic composition is in the form of a dietary supplement comprising the probiotic composition and at least one acceptable excipient.

Particularly, the probiotic composition is in the form of capsules, tablets, pills, sachets, or a suspension (e.g., in an oil). Particularly, the capsule, tablet, or pill have a weight of about 350 mg to about 450 mg, more particularly, 400 mg. Particularly, the sachet has a weight of about 2 g to about 6 g.

In a particular embodiment the probiotic composition is in the form of a vegetable capsule and comprises HMPC.

A food supplement, also known as dietary supplement or nutritional supplement is considered another particular pharmaceutical product. This is a preparation or product intended to supplement the diet, made from compounds usually used in foodstuffs, which provide nutrients or beneficial ingredients that are not usually ingested in the normal diet or may not be consumed in sufficient quantities. Mostly, food supplements are considered as food products, but sometimes they are defined as drugs, natural health products, or nutraceutical products. In the sense of the present invention, food supplements also include nutraceuticals. Food supplements are usually sold "over the counter", i.e., without prescription. If the food supplement adopts the form of a pill, a capsule a tablet or a powder, it comprises excipients which are the same as the used in medicaments. A food supplement however, can also adopt the form of a food product which is fortified with some nutrients (e.g., a bar or yoghurt).

Thus, in a particular embodiment, the probiotic compositions are formulated as a food supplement or dietary supplement. The dietary supplement can be administered as such, can be mixed with a suitable drinkable liquid, such as water, yoghurt, milk or fruit juice, or can be mixed with solid or liquid food. In this context the food supplement can be in the form of tablets or lozenges, pills, capsules, granules, powders, suspensions, sachets, sweets, bars, syrups and corresponding administration forms, usually in the form of a unit dose.

In some embodiments, the probiotic composition is in the form of an oily suspension to be administered alone or mixed with a liquid. The oily suspension comprises at least one edible oil such as olive oil, maize oil, soybean oil, linseed oil, sunflower oil or rice oil. The oil is present in a quantity of at least 70% weight/weight. In a particular embodiment, the oily suspension also comprises at least one excipient which is an emulsifier, stabilizer or anti-caking agent, in an amount of 0.1-15% w/w. Suitable agents are silicon dioxide, silica gel, colloidal silica, precipitated silica, talc, magnesium silicate, lecithin, pectin, starch, modified starches, konjac gum, xanthan gum, gellan gum, carrageenan, sodium alginate, mono- or diglycerides of fatty acids such as glycerol monostearate or glycerol monooleate and citric acid esters of mono- or diglycerides.

Particularly, the probiotic composition is in the form of an infant food supplement in the form of oily suspension. In a particular embodiment the oily suspension comprises sunflower oil and colloidal silica, particularly at 1% by weight, and the bacterial cells.

In another embodiment the oily suspension comprises sunflower oil and an agent selected from lecithin, mono- or diglycerides of fatty acids, carrageenan and sodium alginate, and the bacterial cells.

In some embodiments, the probiotic composition is in the form of an edible product comprising the probiotic composition and at least one edible ingredient. Particularly, the edible product can be a dairy product, milk, yogurt, curd.

The compositions of the invention also can be included in a variety of food products or edible compositions, such as a milk product (a yogurt, a cheese, a fermented milk, a milk powder, a milk based fermented product, an ice-cream, a fermented cereal based product, a milk based powder), bread, bars, spreads, biscuits and cereals, a beverage, different types of oil, or a dressing. The term "food product" is used herein in its broadest meaning, including any type of product, in any form of presentation, which can be ingested by an animal, but excluding pharmaceutical and veterinary products. Examples of other food products are meat products, chocolate spreads, fillings and frostings, chocolate, confectionery, baked goods, sauces and soups, fruit juices and coffee Whiteners. Particularly interesting food products are food supplements and infant formulas. The food product particularly comprises a carrier material such as oat meal gruel, lactic acid fermented foods, resistant starch, dietary fibres, carbo-hydrates, proteins and glycosylated proteins. In a particular embodiment the strains of the invention are encapsulated or coated. Particularly, milks can be either of animal or vegetable origin.

In an embodiment, the probiotic composition is in the form of vegetable capsules (e.g., with hydroxymethylpropyl-cellulose, HMPC) filled with powder containing *L. plantarum* DSM 33765 (e.g., 1 billion lyophilized colony forming units (CFUs)) along with *L. plantarum* CECT 7484, *L. plantarum* CECT 7485 and *P. acidilactici* CECT 7483 (e.g., 1 billion lyophilized CFUs), together with a carrier (e.g., maltodextrin, potato starch, dextrose).

In another embodiment, the probiotic composition is in the form of an aluminum sachet containing the bacterial strains (e.g., in the same amounts described above), a carrier (e.g., maltodextrin, dextrose, rice fiber, potato starch), a sweetener (e.g., sucralose, sodium saccharin) and a flavoring agent.

In another embodiment, the probiotic composition is in the form of a bottle containing the bacterial strains (e.g., in the same amounts described above) in suspension in sunflower oil, to be administered as drops.

In some embodiments, the probiotic composition of the present disclosure is administered immediately after the onset of a disease disclosed herein or after the detection of the infection. In some embodiments, additional doses of the composition of the present disclosure are subsequently administered after an initial dose.

In some embodiments, the probiotic composition is administered in a single dose or repeated dose at specific time intervals, e.g., can be administered daily for a specific number of days or according to a specific dosing schedule. Particularly, the probiotic composition is administered during from 10 days to 90 days. More particularly, it is administered during from 10 days to 60 days or from 15 to 45 days, more particularly during 30 days.

In some embodiments, the probiotic composition is administered from once every three days to thrice a day, particularly, once a day.

In some embodiments, the probiotic composition of the present disclosure can be administered via e.g., oral, intrapulmonary, intravenous, intramuscular, or subcutaneous. Particularly, the probiotic composition is administered orally. In other embodiments, the probiotic composition can be administered by nasal inhalation, oral spray via or nasogastric route.

EXAMPLES

Example 1: Isolation and Characterization of Strain *L. plantarum* CECT 30292 (DSM 33765)

Deposit numbers CECT 30292 and DSM 33765 are used indistinguishably.

1.1. Isolation of the Strain

A novel strain of *L. plantarum* deposited as DSM 33765 was isolated both from humans (fecal sample) and chicory (*Cichorium intybus*) by diluting plant extract on phosphate-buffered saline buffer (PBS), and subsequently seeding on Man-Rogosa-Sharpe agar plates (MRS) and incubating under microaerophilic conditions (5% CO2) at 37° C.

1.2. Whole Genome Sequencing

Strain *L. plantarum* DSM 33765 was grown for 8 h in MRS liquid broth at 37° C. and cells were collected by centrifugation at early log phase. Total genomic and plasmidic DNA was extracted with QIAamp DNA mini kit (Quiagen) following manufacturer instructions, with additional lysis step where the cells were incubated at 37° C. for 10 min in lysis buffer-added lysozyme at 20 mg/mL (Sigma Aldrich, Steinheim am Albuch, Germany) and mutanolysin at 40 U/mL (Sigma Aldrich). Template DNA was prepared with Sequel II Binding Kit 2.0 (Pacific Bioscience), sequenced with PacBioRSII at TAKARA BIO INC (Kaneka, Japan) and assembled with software SMRT Link v8.0.0 (Pacific Bioscience).

Chromosome alignments between DSM 33765 and genome of reference *L. plantarum* WCSF1 strain [Kleerebezem et al. 2003] as well as the genomes of *L. plantarum* CECT 7484, CECT 7485 and ATCC 202195 were performed using the progressive MAUVE algorithm [Darling et al. 2004], Results of whole genome comparison (Table 1) unambiguously show strain DSM 33765 to be of the same species *L. plantarum* as the other strains, based on Average Nucleotide Identity over the whole genome (ANI) of >98.5%, clearly higher than the species boundary of 95% [Jain et al. 2018],

TABLE 1

Whole genome comparison based on ANI

| | Lp_ATCC 202195 | Lp_CECT 7484 | Lp_CECT 7485 | Lp_WCFS1 | Lp_DSM 33765 |
|---|---|---|---|---|---|
| Lp_ATCC | * | 98.61% | 98.64% | 98.61% | 98.64% |
| Lp_CECT 7484 | 98.77% | * | 98.77% | 98.80% | 99.55% |
| Lp_CECT 7485 | 98.83% | 98.83% | * | 98.93% | 98.70% |
| Lp_WCFS1 | 98.68% | 98.80% | 98.76% | * | 98.79% |
| Lp_DSM 33765 | 98.69% | 99.71% | 98.70% | 98.78% | * |

Moreover, tree analysis based on ANI (FIG. 1) shows the strain to belong to the same clade as CECT 7484 (ANI of 99.71%), while being more distantly related to reference strain WCFS1, as well as ATCC 202195 and CECT 7485 (ANI values of 98.7-98.8%).

1.3. Molecular Fingerprinting

Strain DSM 33765 was subjected to a previously described protocol [Rodas et al. 2005] with minor modifications. The strain was grown on MRS agar plates and incubated at 37° C. 5% CO2 for 18 h. Cells were harvested and washed 3 times in 8 ml PET (10 mM Tris pH 7.6, 1 M NaCl) then centrifuged at 6000 rpm 10 min. Pellets were resuspended in 700 ml lysis buffer (6 mM Tris, 1 M NaCl, 0.1 M EDTA, 0.5% SLS, 0.2% deoxycholic acid; 1 mg/ml lysozyme; 40 U/ml mutanolysin; 20 mg/ml RNase). An equal volume of 1.6% low melting point agarose (FMC BioProducts, Rockland, ME, USA) was added to the resuspended cells and solidification was allowed at 4° C. for 1 h. Inserts were transferred to 2 ml lysis buffer II (0.5 M EDTA pH 9.2, 1% N-lauryl sarcosine and 1 mg/ml pronase) and incubated at 50° C. for 48 h. Then, inserts were washed at room temperature with TE buffer (10 mM Tris, 1 mM EDTA pH 8.0). Total DNA digestion was performed by Sma-I restriction enzyme (Roche Diagnostics).

Pulse-field gel electrophoresis (PFGE) was carried out in duplicate using CHEF DRIII apparatus (BioRad Laboratories). Inserts were loaded in a 1% agarose gel (SeaKem ME agarose, FMC BioProducts, ME, USA). DNA MW (molecular weight) markers were Lambda ladder PFG Marker and Low Range PFG Marker (New England Biolabs). After electrophoresis, gels were stained with ethidium bromide and UV using GelDoc System (BioRad).

Results show the *L. plantarum* DSM 33765 strain has a reproducible PFGE profile, which is different than the profile of closely related strain *L. plantarum* CECT 7484. Particularly, compared to CECT 7484, strain DSM 33765 lacks a band of 97 kDa but has additional bands between 48.5 and 32.1 kDa. Hence, albeit closely related, both strains are demonstrated to be different one another.

1.4. Genome Annotation

General genome annotation was performed with software DFAST [Tanizawa et al. 2018] including the tRNAscan and Prodigal features, and the Conserved Domain Database [Shennan et al. 2020] Plasmids were identified using PlasmidDB software [Galata et al. 2019], In order to identify the presence of possible antibiotic resistance (AR) genes, the genome of *L. plantarum* DSM 33765 was compared against the last version of the Comprehensive Antibiotic Resistance Database (CARD), a bioinformatic database of resistance genes, their products, and associated phenotypes [Alcock et al. 2020] using the Resistance Gene Identifier (RGI), which supports analysis of whole genomes, using default parameters. As a double-check, the genome sequence was also compared against the last version of ResFinder database [Bortolaia et al. 2020], Results are shown in Table 2. PacBio sequencing of *L. plantarum* DSM 33765 resulted in four contigs comprising 3,322,082 bp. While the larger contig (3,237,983 bp) was identified as the chromosomic sequence, the three additional contigs (41,908 bp, 35,007 bp and 7,184 bp) were found to correspond to different *L. plantarum* plasmids.

No antibiotic resistance genes were found either in the bacterial chromosome or in the three plasmids. Two pilin genes and ten mucin-binding genes were identified, highlighting the adaptation of the strain to bind to mucus and epithelium and thus supporting its capacity to colonize the intestine.

TABLE 2

Characterization of *L. plantarum* DSM 33765 genome

| Contig | Length (bp) | tRNA genes | rRNA genes | Predicted genes (CDS) | AR genes | Mucin-binding and pilin genes | Molecule (Accession Num) |
|---|---|---|---|---|---|---|---|
| 1 SEQ ID NO: 5 | 3,237,983 | 76 | 46 | 3390 | None | 10 + 2 | Chromosome |
| 2 SEQ ID NO: 6 | 41,908 | 0 | 0 | 52 | None | None | Plasmid (CP017381.1 |
| 3 SEQ ID NO: 7 | 35,007 | 0 | 0 | 63 | None | None | Plasmid (CP050806.1 |
| 4 SEQ ID NO: 8 | 7,184 | 0 | 0 | 6 | None | None | Plasmid (CP028984.1 |
| Total | 3,322,082 | 76 | 46 | 3511 | None | 10 + 2 | |

1.5. Resistance to Gastric Conditions of Strain CECT 30292

Simulated gastric medium was prepared containing 7.3 g/L of sodium chloride, 0.5 g/L of potassium chloride, 3.8 g/L of sodium hydrogen carbonate and 3 g/L of pepsin in distilled water. Samples of said simulated medium were adjusted to pH 2.3 and to pH 3 using hydrogen chloride 1 N. 0.1 mL of overnight cultures of strain CECT 30292 were inoculated into 10 mL of simulated gastric medium at pH 2.3 or pH 3, thoroughly mixed and incubated for 30 min or 90 min at 37° C. Subsequently, 10-fold serial dilutions were prepared in buffered saline medium. Both 0.1 mL of the overnight culture and 0.1 mL of various serial dilutions were seeded into different MRS agar plates each. Colonies were counted after incubating at 37° C. for 48 h under anaerobic conditions. The experiment was performed in quadruplicate.

Results in Table 3 below show the strain is highly resistant to exposure to gastric medium:

| Condition | Inoculated cells log (CFUs/mL) | Surviving cells log (CFUs/mL) | Percent of survival (on absolute counts) |
|---|---|---|---|
| pH 2.3 for 30 minutes | 7.50 ± 0.02 | 7.45 ± 0.02 | 88.1% |
| pH 3.0 for 90 minutes | 7.48 ± 0.06 | 7.43 ± 0.10 | 87.6% |

Example 2: Clinical Study 2.1. Study Product

Vegetable capsules (hydroxymethylpropyl-cellulose, HMPC) were filled with powder containing 1 billion lyophilized cfus of novel strain *L. plantarum* DSM 33765 along with 1 billion lyophilized cfus of strains *L. plantarum* CECT 7484, *L. plantarum* CECT 7485 and *P. acidilactici* CECT 7483, together with a maltodextrin carrier. CFU load of the capsules was verified by serial dilution in PBS buffer followed by seeding in MRS agar and counting of colonies after 48 h of incubation at 37° C. under microaerophilic conditions.

2.2. Study Design

A quadruple blinded (patient, care provider, outcomes assessor and main investigator), randomized clinical trial was conducted against placebo to evaluate safety and efficacy of the combination of strain *L. plantarum* DSM 33765 and strains *L. plantarum* CECT 7484, *L. plantarum* CECT 7485 and *P. acidilactici* CECT 7483, at a total dose of 2 billion CFUs once daily in subjects with mild COVID-19. The trial adhered to the ethical tenets of the Declaration of Helsinki.

The primary aim was to improve COVID-19 severity, according to the World Health Organization scale [WHO Working Group. 2020], The secondary aims were to evaluate the effect of the above-mentioned combination in the reduction of the frequency and severity of individual COVID-19 symptoms, the reduction of viral load and the increase in levels of immunoglobulin antibodies IgG and IgM. 300 adults, aged 18 to 60 years, with positive nasopharyngeal detection of SARSCoV-2 with Real-Time Polymerase Chain Reaction method (PCR), with mild symptoms of COVID-19 (as per WHO COVID-19 severity scale) and providing written informed consent, were randomized. Individuals with blood oxygen saturation (SpO2)<90%, taking immunosuppressants, having acute pancreatitis or having regularly used other probiotics within two weeks of study initiation were excluded from participating. Randomization was performed according to a computer-generated list and all study participants (patients, care providers, outcomes assessor and main investigator) were blinded to whether they had been assigned to placebo or probiotic capsules. Probiotic and placebo capsules were indistinguishable one another. The computer-generated list was kept locked and in a sealed envelope by a pharmacist not participating in the study.

Individuals randomized to either probiotic or placebo were administered one capsule of their assigned intervention once daily for 30 consecutive days. COVID-19 symptoms were evaluated every 5 days. Quantification of SARSCoV-2 viral load in nasopharyngeal swabs was performed on days 0, 15 and 30 of the intervention. Quantification of specific IgG and IgM antibodies against SARSCoV-2 was performed in blood samples on days 0, 15 and 30 of the intervention.

2.3. Characteristics of the Subjects Recruited at Baseline

The probiotic and placebo groups in the study were balanced regarding clinical and demographic characteristics at baseline (Table 4).

TABLE 4

Characteristics of subjects at baseline.

| Characteristics of subjects at baseline | Probiotic (n = 150) | Placebo (n = 150) |
|---|---|---|
| Mild COVID-19 symptoms (n, %) | 150 (100) | 150 (100) |
| Women (n, %) | 82 (54.7) | 79 (52.7) |
| Age (median, min-max) | 34 (19-60) | 39 (18-59) |
| Days since onset of symptoms | 4.6 ± 2.9 | 5.3 ± 3.9 |
| Blood Group | | |
| O+ (n, %) | 66 (44.0) | 55 (38.7) |
| A+ (n, %) | 48 (32.0) | 52 (34.7) |
| B+ (n, %) | 16 (10.7) | 14 (9.3) |
| Other (n, %) | 20 (13.3) | 29 (17.3) |
| Smoker (n, %) | 22 (14.7) | 20 (13.3) |
| Diabetes (n, %) | 15 (10.0) | 16 (10.7) |
| Hypertension (n, %) | 28 (18.7) | 31 (20.7) |
| Body Mass Index in $Kg/m^2$ (Average ± SD) | 27.7 ± 4.9 | 29.6 ± 3.9 |
| Days since symptoms started (Average ± SD) | 3.9 ± 1.3 | 4.0 ± 1.3 |
| Viral load as Log of Copies/pl (Average ± SD) | 3.7 ± 0.22 | 3.8 ± 0.21 |
| SARSCoV-2 IgG in U/ml (Average ± SD) | 9.2 ± 7.1 | 8.3 ± 6.4 |
| SARSCoV-2 IgM in U/ml (Average ± SD) | 18.0 ± 3.7 | 18.0 ± 2.7 |
| Fever (n, %) | 73 (48.7) | 67 (44.7) |
| Mild | 23 (15.3) | 23 (15.3) |
| Moderate to severe | 50 (33.4) | 44 (29.4) |
| Cough (n, %) | 115 (76.7) | 111 (74.0) |
| Mild | 28 (18.7) | 22 (14.7) |
| Moderate to severe | 87 (58.0) | 89 (59.3) |
| Headache (n, %) | 109 (72.7) | 110 (73.3) |
| Mild | 6 (4.0) | 7 (4.7) |
| Moderate to severe | 103 (68.7) | 104 (69.3) |
| Shortness of breath (n, %) | 46 (30.7) | 30 (20.0) |
| Mild | 39 (26.0) | 27 (18.0) |
| Moderate to severe | 7 (4.7) | 3 (2.0) |
| Bodily pain (n, %) | 69 (46.0) | 78 (52.0) |
| Mild | 22 (14.7) | 28 (18.7) |
| Moderate to severe | 47 (31.3) | 50 (33.3) |
| Oxygen saturation (n, %) | | |
| $SpO_2$ > 92% | 21 (14.0) | 35 (23.3) |
| $SpO_2$ 90 to 92% | 129 (86.0) | 115 (76.7) |

SD = Standard Deviation.

2.4. Results

During the 30-day intervention, only 3 subjects dropped from the study in the probiotic group and 4 in the placebo group. No patients died or required Intensive Care Unit during the 30-day intervention.

Complete remission of COVID-19: Complete remission of COVID-19 is defined as complete disappearance of symptoms along with a negative PCR result (i.e., a score of zero in the WHO COVID-19 severity scale). No patients displayed complete remission on day 15 of the intervention. However, a much higher number of patients displayed complete remission in the probiotic group than in the placebo group on day 30 of the intervention, the difference being highly statistically significant (p-value <0.001, as per a Chi-squared test). See Table 5.

Symptomatic remission: Symptomatic remission was defined as complete disappearance of symptoms regardless of PCR result (i.e., a score of zero or one in the WHO COVID-19 severity scale). Patients receiving probiotic displayed remission at earlier stages of the intervention (i.e., days 10, 15 15 and 20) than those receiving placebo. See Table 5.

TABLE 5

Complete remission of COVID-19 and symptomatic remission.

| | Probiotic | Placebo |
|---|---|---|
| Complete Remission | | |
| Day 15 (n, %) | 0 (0.0) | 0 (0.0) |
| Day 30 (n, %) | 82 (55.8)* | 41 (28.1)* |
| Symptomatic Remission | | |
| Day 5 (n, %) | 0 (0.0) | 0 (0.0) |
| Day 10 (n, %) | 42 (28.0)* | 13 (8.7)* |
| Day 15 (n, %) | 126 (84.0)* | 82 (54.7)* |
| Day 20 (n, %) | 150 (100.0)* | 127 (85.2)* |
| Day 25 (n, %) | 148# (100.0) | 145 (98%) |
| Day 30 (n, %) | 147# (100.0) | 146# (100%) |
| Requiring Intensive Care Unit or death (n, %) | 0 (0.0) | 0 (0.0) |

#Updated total number of subjects considering subjects dropping the study at different evaluation days.
*Statistically significant at p-value < 0.001.

Figure 3:
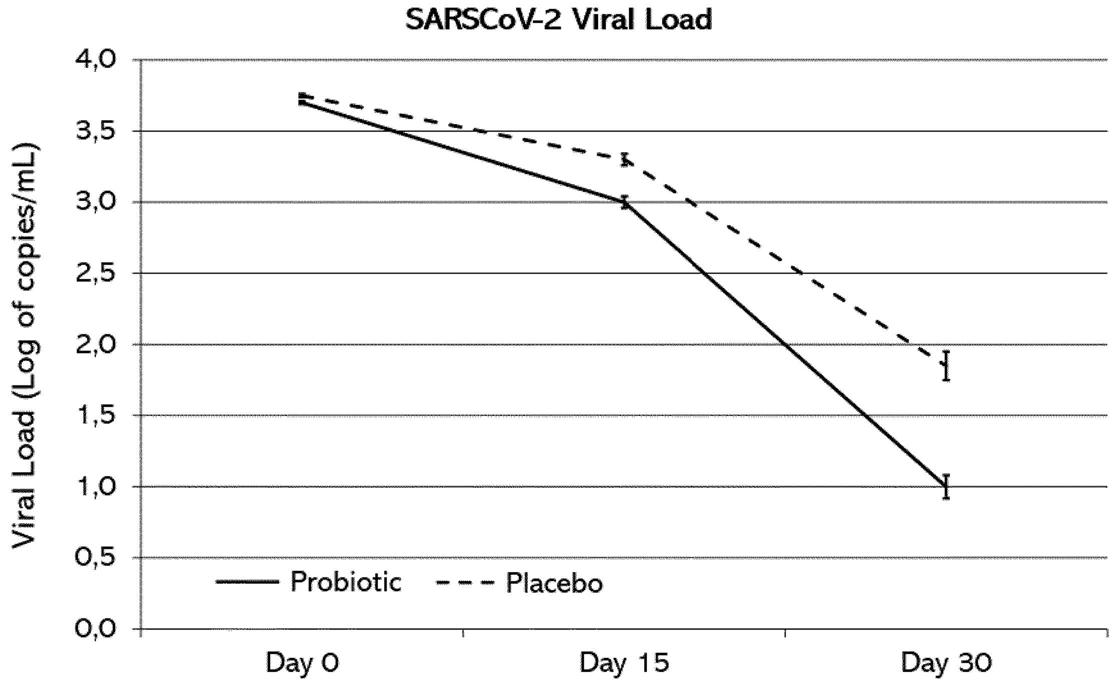
FIG. 3 shows the concentration of the viral load of SARS-CoV-2 in nasopharyngeal swabs at days 0, 15 and 30 of intervention for Probiotic and Placebo group. At day 30, the difference averaged 0.9 log, thus concentration was reduced 9 times on average. See working Example herein for further details.

Viral load: During the 30-day intervention, the concentration of the viral load in nasopharyngeal swabs was further reduced in the probiotic group than in the placebo group, the difference being highly statistically significant (p<0.001, as per repeated measures ANOVA), as can be seen FIG. 3. At the end of the 30-day intervention, the difference averaged 0.9 log, thus concentration was 25 reduced 9 times on average.

Figure 4:
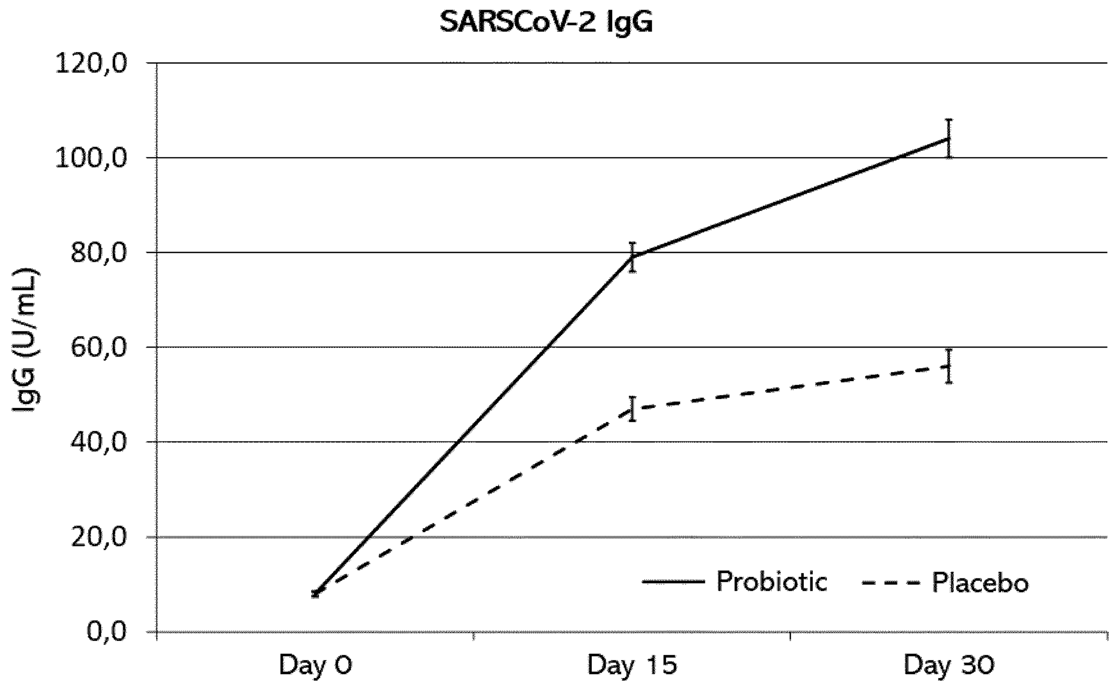
FIG. 4 shows the concentration of IgG and IgM antibodies against SARS-CoV-2 at days 0, 15 and 30 of intervention for Probiotic and Placebo group. At day 30, subjects receiving probiotic had IgG levels twice as high as those of subject in placebo group. See working Example herein for further details.
Figure 4:
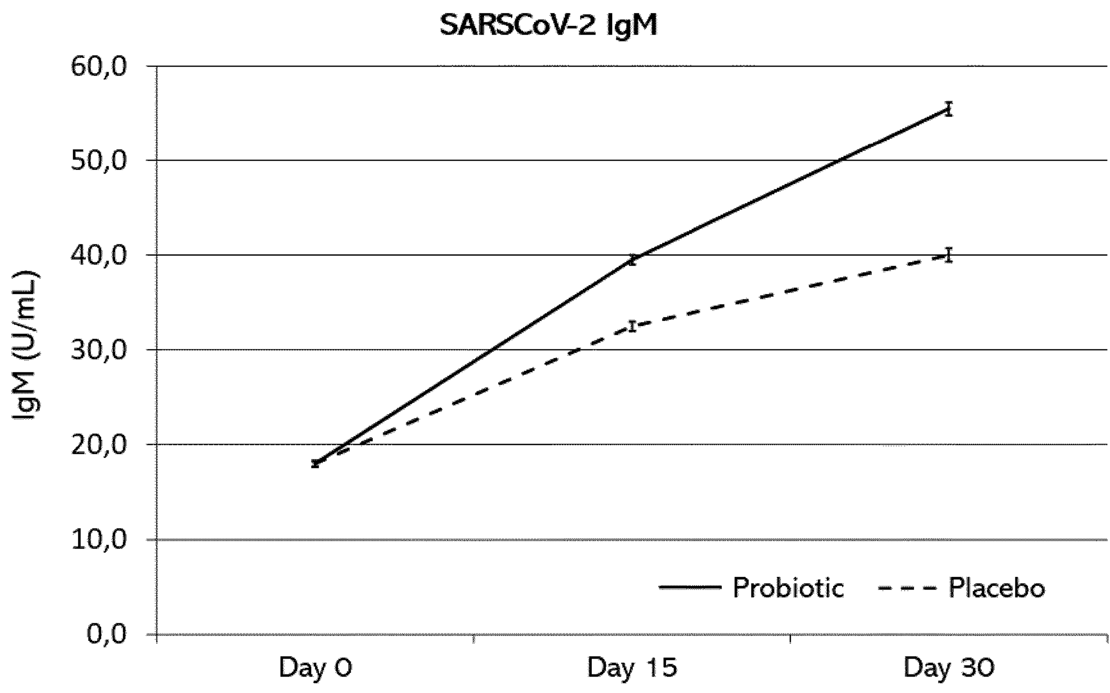

Concentration of IG and IM antibodies: During the 30-day intervention, the concentration of IgG and IgM antibodies against SARS-CoV-2 was further increased in the probiotic group than in the placebo group, the difference being highly statistically significant (p<0.001, as per repeated measures ANOVA), as can be seen in FIG. 4. At the end of the 30-day intervention, subjects receiving probiotic had IgG levels twice as high as those of subject in placebo group.

Statistical adjustments were performed to assess whether age, blood group, body mass index, concurrent diabetes or concurrent hypertension modulated the effect of the probiotic on remission rate, viral load and antibody levels. Remarkably, none of these variables were found to modulate the effect of the probiotic intervention. Therefore, probiotic achieved its beneficial effect regardless of age, blood group, body mass index, concurrent diabetes or concurrent hypertension.

Reduction of specific symptoms of COVID-19: During the 30-day intervention, probiotic intervention was also found to significantly reduce the duration of various specific symptoms of COVID-19, compared to placebo, as well as the days with blood oxygen saturation below 92% (hypoxemia), the later despite a higher proportion of subjects with saturation below 92% at baseline in the probiotic group (all with p<0.05, as per Mann-Whitney test). See Table 6.

TABLE 6

| Reduction of specific symptoms of COVID-19 | | | |
|---|---|---|---|
| Symptoms | Probiotic | Placebo | P-value |
| Fever (mean, SD) | 9.2 ± 3.9 | 10.8 ± 4.6 | 0.005 |
| Cough (mean, SD) | 10.1 ± 4.7 | 13.5 ± 6.5 | 0.001 |
| Headache (mean, SD) | 6.9 ± 4.0 | 10.6 ± 6.5 | 0.001 |
| Shortness of breath (mean, SD) | 1.1 ± 1.6 | 2.2 ± 3.1 | 0.021 |
| Bodily pain (mean, SD) | 2.9 ± 2.8 | 5.0 ± 4.4 | 0.001 |
| Oxygen saturation (SpO2) < 92% (mean, SD) | 7.4 ± 3.6 | 8.4 ± 4.0 | 0.036 |
| Diarrhea (mean, SD) | 1.8 ± 2.8 | 4.4 ± 6.4 | 0.010 |

Example 3: Serum Concentration Measurement of Interferon-Beta (IFNb) and Chemokine CXCL13

3.1. Methods 70 individuals were randomly chosen from the 300 individuals described in EXAMPLE 2. Randomization was primarily stratified by intervention group to ensure that 35 individuals corresponded to placebo group and 35 to probiotic group as well as by lung infiltration status at the beginning of the intervention and by responder status at the end of the intervention, in order to ensure that the selected subpopulation of 70 individuals had a similar distribution than the full population of 300 individuals.

Stored, frozen serum samples taken on days 0, 15 and 30 of intervention (See EXAMPLE 2) were used to measure interferon-beta (IFNb) and the chemokine CXCL13 using standard Enzyme-Linked ImmunoSorbent Assay (ELISA) laboratory kits. Digital lung X-ray scans taken on days 0, 15 and 30 were also retrieved from patients records, and lung inflammatory infiltrates were scored, whenever present, using the validated Brixia score (the higher the score, the more severe the inflammatory infiltrate) [Borghesi et al., 2020], 3.2. Results Clinical characteristics of the subjects: The probiotic and placebo groups in the subpopulation of 70 subjects were balanced regarding clinical and demographic characteristics at baseline (Table 7).

TABLE 7

| Characteristics of the 70 subjects at baseline. | | |
|---|---|---|
| | Probiotic (n = 35) | Placebo (n = 35) |
| Women (n, %) | 22 (62.9%) | 22 (62.9%) |
| Age (Average ± SD) | 36.1 ± 12.0 | 38.3 ± 14.4 |
| Number of metabolic comorbidities [median, range]* | 0 [0-2] | 0 [0-3] |
| Days since symptom onset (Average ± SD) | 4.1 ± 1.2 | 3.9 ± 1.3 |
| Viral load as Log of Copies/ml (Average ± SD) | 6.7 ± 0.3 | 6.8 ± 0.2 |
| SARSCoV-2 IgG in U/ml (Average ± SD) | 9.9 ± 7.5 | 7.7 ± 6.6 |
| SARSCoV-2 IgM in U/ml (Average ± SD) | 17.6 ± 3.8 | 18.3 ± 2.6 |
| Presence of lung infiltrates (n, %) | 15 (42.9%) | 11 (31.4%) |

*Comprising diabetes, arterial hypertension and obesity (i.e., body mass index ≥ 30 $Kg/m^2$)
SD = Standard Deviation.

Figure 5:
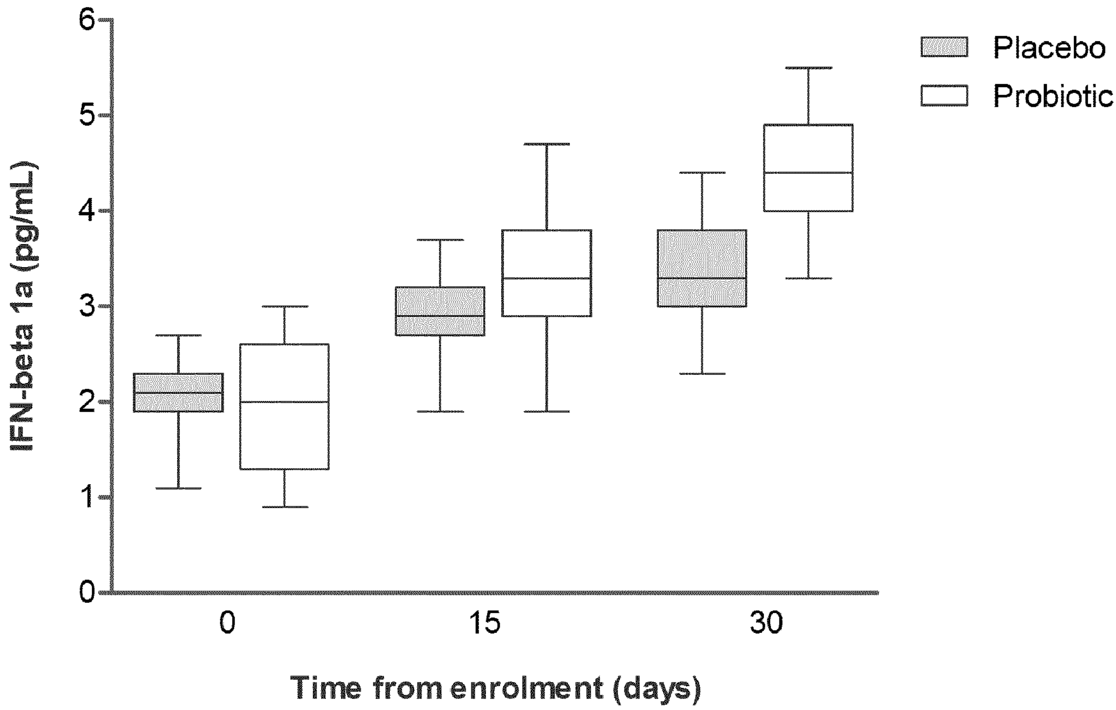
FIG. 5 shows serum concentration of interferon-beta 1a (INFb) at days 0, 15 and 30 of intervention for Probiotic and Placebo group. At day 30, subjects receiving probiotic had INFb levels significantly increased with respect to the placebo group. See working Example herein for further details.

Serum concentration of interferon-beta: At baseline, the levels of IFNb were indistinguishable between probiotic and placebo groups. During the 30-day intervention, the levels of IFNb were significantly increased in probiotic group compared to placebo (p<0.001, repeated-measures ANOVA) as seen in FIG. 5. More precisely, concentration in probiotic group was significantly higher both on day 15 and on day 30 compared to placebo (p<0.05).

Figure 6:
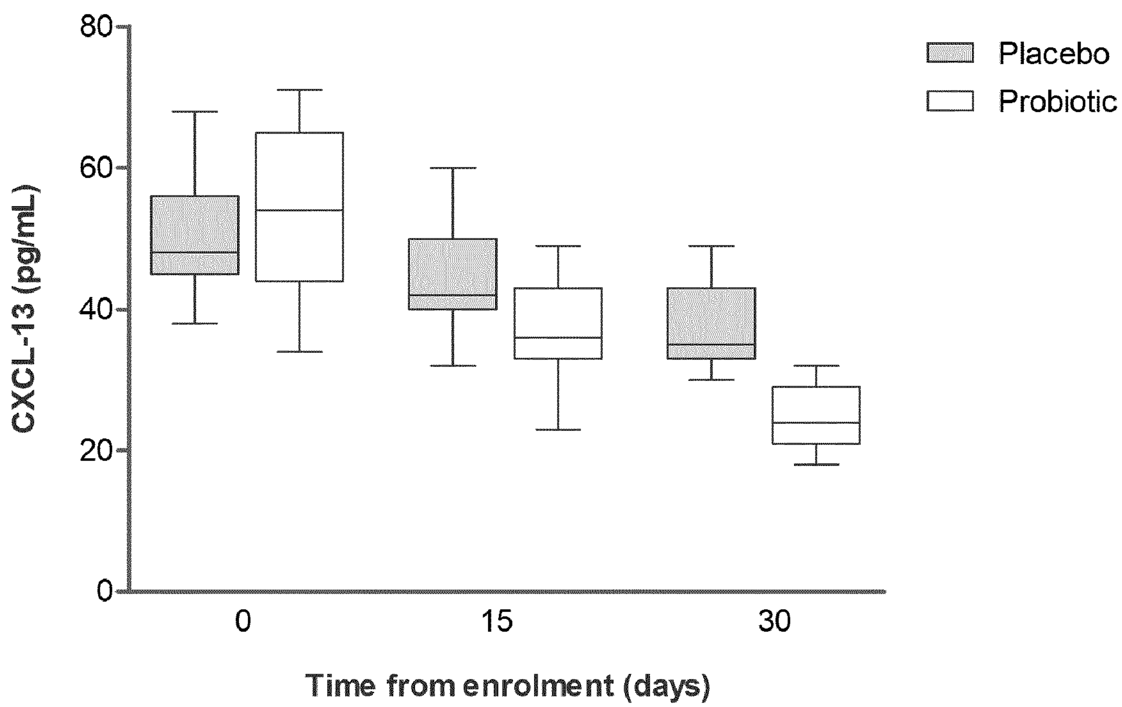
FIG. 6 shows serum concentration of CXCL13 at days 0, 15 and 30 of intervention for Probiotic and Placebo group. Concentration in probiotic group was significantly lower both on day 15 and on day 30 compared to placebo. See working Example herein for further details.

Serum concentration of CXCL13: At baseline, the levels of CXCL13 were indistinguishable between probiotic and placebo groups. During the 30-day intervention, the levels of CXCL13 were significantly reduced over time in the probiotic group compared to placebo (p<0.001, repeated-measures ANOVA) as seen in FIG. 6. More precisely, concentration in probiotic group was significantly lower both on day 15 and on day 30 compared to placebo (p<0.05).

Clearance of symptoms: The 70 subjects reported daily their symptoms in a patient electronic diary. The duration of several symptoms was significantly shorter in probiotic group compared to placebo group, as indicated in Table 8.

TABLE 8

| Duration of various viral infection symptoms (average and standard deviation). | | | |
|---|---|---|---|
| | Probiotic (n = 35) | Placebo (n = 35) | P-value (Student T test) |
| Days with fever (>37.5° C.) | 3.6 ± 3.5 | 6.1 ± 3.4 | p = 0.003 |
| Days with cough | 9.4 ± 4.9 | 12.7 ± 6.3 | p = 0.016 |
| Days with headache | 6.0 ± 4.0 | 9.1 ± 6.6 | p = 0.023 |
| Days with body aches | 1.7 ± 2.5 | 4.4 ± 4.1 | p = 0.001 |

As a further confirmation of the positive role of type-1 interferons against viral infection, higher levels of interferon-beta correlated to less days with fever (Spearman correlation=−0.24, p-value=0.042) and less days with cough (Spearman correlation=−0.26, p-value=0.033) in the overall population of 70 subjects. A similar trend (i.e., a p-value above 0.05 but below 0.10) was also observed for body aches (Spearman correlation=−0.21, p-value=0.075). Moreover, lower levels of CXCL13 also correlated to less days with fever (Spearman correlation=0.27, p-value=0.024).

In the subgroup of patients with lung inflammatory infiltrates at baseline (n=15 in probiotic and n=11 in placebo), decrease in infiltration correlated to higher interferon-beta (Spearman correlation=0.46, p-value=0.018) and especially lower CXCL13 (Spearman correlation=0.69, p<0.001), in agreement with the protective effect of lowering CXCL13 for reducing lung inflammation.

Viral clearance: All 70 subjects were positive for SARS-CoV2 at the beginning of the intervention by PCR analysis (see EXAMPLE 2). At the end of the 30-day intervention, 17 of 35 subjects (48.6%) in the probiotic group and 8 of 35 (22.9%) in the placebo group had achieved a complete viral remission by PCR analysis. Therefore, the effect of the probiotic was more than twice as high that of the placebo, this difference being statistically significant (Chi-squared test p-value=0.026).

Example 4: Serum Concentration Measurement of Plantaricin G 4.1. Methods

*L. plantarum* strains (CECT 30292, CECT 7483, CECT 7484, CECT 7485, CECT 7481, 299v and WCFS1) were grown in MRS broth at 37° C. Bacterial cells were collected at the exponential phase (OD62o~0.6) and at the stationary state (OD62o>1.5) by centrifugation.

Total RNA was isolated from pellets using RNeasy Mini Kit according to manufacturers' protocol. RNA was then converted to cDNA using NxGen Reverse Transcriptase Kit. Real-Time Quantitative Polymerase Chain Reaction (RT-qPCR) was performed using SYBRGreen on an AB17900 machine and Cycle Threshold (Ct) values were recorded. Data was normalized with the housekeeping gene RecA and expression of the WCSF1 type strain was used as reference to express gene expression using the delta-delta Ct method. RT-qPCR primers used in the experiments are indicated in Table 9.

TABLE 9

RT-qPCR primers used in the experiments.

| Gene | Forward Primer (5'-3') | Reverse Primer (5'-3') |
|---|---|---|
| plnG (target) | AAGTTGACGAGATGGACT (SEQ ID NO: 1) | GTAGTCCCTTCTAAACTCGT (SEQ ID NO: 2) |
| RecA (housekeeping) | GGCAGAACAGATCAAGGAAG G (SEQ ID NO: 3) | TATCCACTTCGGCACGCTTA SEQ ID NO: 4) |

4.2. Results

Figure 7:
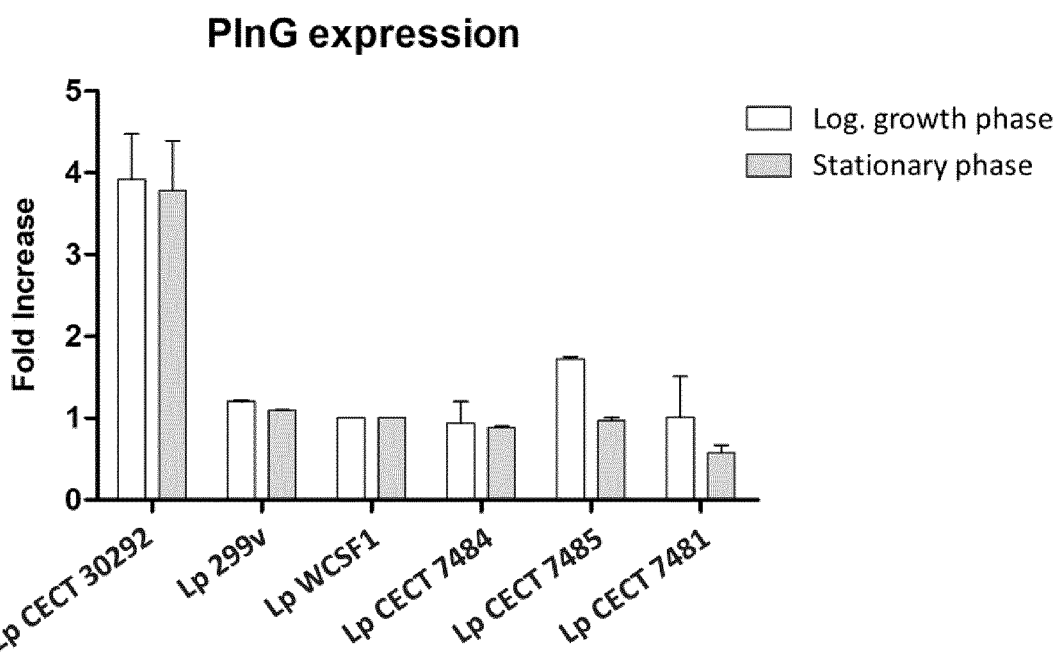
FIG. 7 shows the fold increase of the Plantaricin G (PlnG) protein of *L. plantarum* strains CECT 30292, CECT 7483, CECT 7484, CECT 7485, CECT 7481,299v and WCFS1. *L. plantarum* CECT 30292 significantly overexpresses the plnG gene in comparison to the strain type WCFS1 and also in comparison to all other tested strains. See working Example herein for further details.

RT-qPCR experiments revealed that *L. plantarum* CECT 30292 significantly overexpresses the plnG gene in comparison to the strain type WCFS1 (four-fold increase, p<0.001) and in comparison to all other tested strains (p<0.05). The effect is consistent both when the strain is in exponential growth phase and in stationary state (FIG. 7). Therefore, strain *L. plantarum* CECT 30292 has a higher potential to be sensed by immune cells than other *L. plantarum* strains.

Example 5: Intra-Strain Variability Assessment 5.1. Methods

To assess intra-strain variability, whole-genome sequencing was performed for two different batches of strain DSM 33765 using the same methods already described in EXAMPLE 1.

5.2. Results

The pairwise Average Nucleotide Identity (ANI) between the genomes of two different batches of the same strain (DSM 33765) was 99.99%. Considering the size of the genome of this strain is 3,322,082 base-pairs, this 0.01% difference amounts to up to around 330 nucleotide polymorphisms.

Example 6: PlnG Gene Copies 6.1. Methods

The sequence of the plantaricin G gene (plnG) was downloaded from the UniProt database (https://_www_.uniprot._org/uniprot/Q1WFD0, UniProtKB—Q1WFD0 (Q1WFD0_LACPN), Entry version 73, 29 Sep. 2021) and searched against the genomes of *L. plantarum* strains CECT 7484, CECT 7485, DSM 33765, as well as the reference strain WCSF1 (see EXAMPLE 1). Search was performed using the "tblastn" application from the BLAST program (https://blast.ncbi.nlm.nih.gov/Blast.cgi?PAGE_TYPE=BlastDocs&DOC_TYPE= Download).

6.2. Results

The bacterial chromosomes of the four *L. plantarum* strains analyzed contain one copy of the Plantaricin G (plnG) gene. Remarkably, strain DSM 33765 was the only strain to also contain plasmids carrying the plnG gene, as shown in Table 10 below. This could explain the markedly higher Plantaricin G expression achieved by this strain (EXAMPLE 4).

TABLE 10 plnG gene copies and plasmids with additional plnG gene copies of the analyzed strains.

| Strain | plnG gene copies in | Plasmids with additional plnG |
|---|---|---|
| CECT 7484 | 1 | None |
| CECT 7485 | 1 | None |
| DSM 33765 | 1 | Yes |
| WCSF1 | 1 | None |

REFERENCES https://clinicaltrials.gov/ct2/show/NCT04517422WO2011092261A1

Chong et al. *Lactobacillus plantarum* DR7 improved upper respiratory tract infections via enhancing immune and inflammatory parameters: A randomized, double-blind, placebo-controlled study. J. Dairy Sci. 2019. 102:4783-4797

Meijerink et al. Identification of Genetic Loci in *Lactobacillus plantarum* That Modulate the Immune Response of Dendritic Cells Using Comparative Genome Hybridization. PLoS One 2010. 5:e10632

D'Ettorre et al. Challenges in the Management of SARS-CoV2 Infection: The Role of Oral Bacteriotherapy as Complementary Therapeutic Strategy to Avoid the Progression of COVID-19. Front Med (Lausanne) 2020.:389

Hishiki et al. A Double-Blind, Randomized, Placebo-Controlled Trial of Heat-Killed *Pediococcus acidilactici* K15 for Prevention of Respiratory Tract Infections among Preschool Children. Nutrients 2020. 12(7):1989

Hill et al. The International Scientific Association for Probiotics and Prebiotics consensus statement on the scope and appropriate use of the term probiotic. Nat Rev Gastroenterol Hepatol 2014. 11:506-14

Channapannavar et al. IFN-I response timing relative to virus replication determines MERS coronavirus infection outcomes. J Clin Invest 2019; 129:3625-3639

Haagmans et al. Pegylated interferon-alpha protects type 1 pneumocytes against SARS coronavirus infection in macaques. Nat Med. 2004; 10290-3

Kleerebezem et al. Complete genome sequence of *Lactobacillus plantarum* WCFS1. Proc Natl Acad Sci USA. 2003. 100(4):1990-5

Darling et al. Mauve: multiple alignment of conserved genomic sequence with rearrangements. Genome Res 2004. 14(7): 1394-403

Jain et al. High throughput ANI analysis of 90K prokaryotic genomes reveals clear species boundaries Nat Commun. 2018 Nov. 30; 9(1):5114

Rodas et al. Polyphasic study of wine *Lactobacillus* strains: taxonomic implications. Int J Syst Evol Microbiol 2005. 55(Pt 1):197-207

Tanizawa et al. DFAST: a flexible prokaryotic genome annotation pipeline for faster genome publication. Bioinformatics 2018. 34(6):1037-1039

Shennan et al. CDD/SPARCLE: the conserved domain database in 2020. Nucleic Acids Res 2020. 48:D265-D8

Galata et al. PLSDB: a resource of complete bacterial plasmids. Nucleic Acids Res. 2019. 74:D195-D202

Alcock et al. CARD 2020: Antibiotic Resistome Surveillance with the Comprehensive Antibiotic Resistance Database. Nucleic Acids Research 2020. 48:D517-D525

Bortolaia et al. ResFinder 4.0 for predictions of phenotypes from genotypes. Journal of Antimicrobial Chemotherapy 2020. 75:3491-3500

WHO Working Group. A minimal common outcome measure set for COVID-19 clinical research. Lancet Infect Dis 2020. 20:e192-el97

Borghesi et al. Chest X-ray severity index as a predictor of in-hospital mortality in coronavirus disease 2019: A study of 302 patients from Italy. Int. J. Infect Dis 2020; 96:291-293

SEQUENCE LISTING

The patent contains a lengthy sequence listing. A copy of the sequence listing is available in electronic form from the USPTO web site (https://seqdata.uspto.gov/docdetail?docId=US12734201B2). An electronic copy of the sequence listing will also be available from the USPTO upon request and payment of the fee set forth in 37 CFR 1.19(b)(3).

The invention claimed is:

1. A probiotic composition, comprising: *Lactobacillus plantarum* strain deposited under the Budapest Treaty in the Spanish Type Culture Collection (CECT) under accession number CECT 30292, wherein the probiotic composition is a solid composition, comprising:

a freeze-dried bacterial biomass comprising from about $10^5$ cfu to about $10^{12}$ cfu of the strain; a cryoprotectant; and, a pharmaceutically acceptable carrier chosen from an emulsion, a suspension, a gel, a paste, granules, a powder, and a gum.

2. The probiotic composition according to claim 1, further comprising *Lactobacillus plantarum* CECT 7484, *Lactobacillus plantarum* CECT 7485, and *Pediococcus acidilactici* CECT 7483.

3. A method for obtaining a mutant strain of *Lactobacillus plantarum* strain deposited under CECT 30292, comprising the following steps:

(i) making mutants of *L. plantarum* CECT 30292;

(ii) analyzing the in step (i) obtained mutants and identifying a mutant strain that retains or improves at least one ability of the deposited strain; and, (iii) isolating the in step (ii) identified mutant strain to thereby obtain the mutant strain of *L. plantarum* CECT 30292, wherein the mutant strain retains or improves at least one ability of the deposited strain.

* * * * *